United States Patent [19]

Koshihara et al.

[11] Patent Number: 4,872,762
[45] Date of Patent: Oct. 10, 1989

[54] METHOD AND APPARATUS FOR DETECTING DEFECTIVE PORTION ON INNER SURFACE OF PIPE

[75] Inventors: Toshio Koshihara; Rokurou Misawa; Yuzo Sagawa; Kimio Takehara; Yuji Matoba; Koji Ishihara, all of Tokyo, Japan

[73] Assignee: NKK Corporation, Tokyo, Japan

[21] Appl. No.: 227,366

[22] Filed: Aug. 2, 1988

[30] Foreign Application Priority Data

Aug. 25, 1987 [JP] Japan ................................. 62-209309
Aug. 25, 1987 [JP] Japan ................................. 62-209310
Nov. 6, 1987 [JP] Japan ................................. 62-279321
Dec. 3, 1987 [JP] Japan ................................. 62-304418
Dec. 16, 1987 [JP] Japan ................................. 62-190034
Jan. 13, 1988 [JP] Japan ................................... 63-5397

[51] Int. Cl.$^4$ ............................................. G01N 25/72
[52] U.S. Cl. ....................................... 374/5; 374/44; 374/124; 374/141; 374/137; 250/330; 356/43; 358/100; 358/107; 358/113
[58] Field of Search ...................... 374/5, 30, 44, 137, 374/106, 124, 50, 141, 17; 250/330; 356/43, 51; 358/100, 107, 113

[56] References Cited

U.S. PATENT DOCUMENTS

| | | | |
|---|---|---|---|
| 3,020,745 | 2/1962 | Sielicki | 374/5 |
| 3,504,524 | 4/1970 | Maley | 374/124 |
| 3,566,669 | 3/1971 | Lawrence et al. | 374/5 |
| 4,391,323 | 7/1983 | Schnier | 219/347 |
| 4,395,380 | 7/1983 | Rosh | 374/124 |
| 4,675,512 | 6/1987 | Doucet et al. | 219/535 |

OTHER PUBLICATIONS

McLaughlin, D. V., et al., "Non-Destructive Examination of Fibre Composite Structures by Thermal Field Techniques", NDT International, Apr. 1980, pp. 56-62.
Pollack, Frank G., et al., "Surface Temperature Mapping with Infrared Photographic Pyrometry", NASA Tech. Brief No. 69-10113, Jun. 1969.

Primary Examiner—William A. Cuchlinski, Jr.
Assistant Examiner—Diego F. F. Gutierrez
Attorney, Agent, or Firm—Frishauf, Holtz, Goodman & Woodward

[57] ABSTRACT

A method and an apparatus for detecting a defective portion on the inner surface of a pipe, the outer surface of which is exposed, includes: heating or cooling a pipe, the outer surface of which is exposed, from the side of the outer surface thereof so that a difference in temperature is produced between a portion of the outer surface of the pipe corresponding to an accumulation of foreign matters or a thinner portion as a defective portion on the inner surface thereof, and a portion of the outer surface of the pipe corresponding to a normal portion of the inner surface thereof; then shooting the outer surface of the pipe by means of a thermal imaging system while the above-mentioned difference in temperature still remains on the outer surface of the pipe to obtain a thermal image of the difference in temperature; and detecting the accumulation of foreign matters or the thinner portion as the defective portion of the inner surface of the pipe by means of the thus obtained thermal image.

10 Claims, 14 Drawing Sheets

FIG. 8
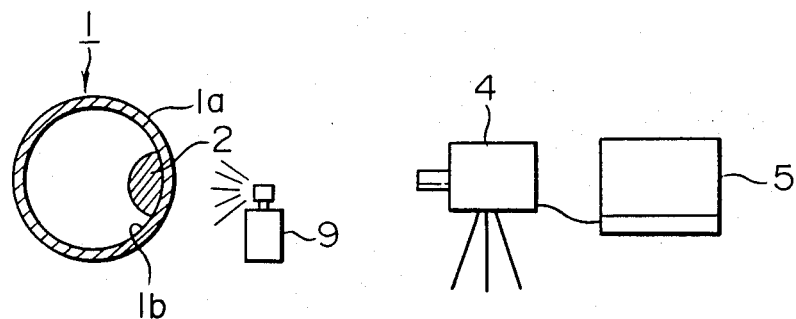
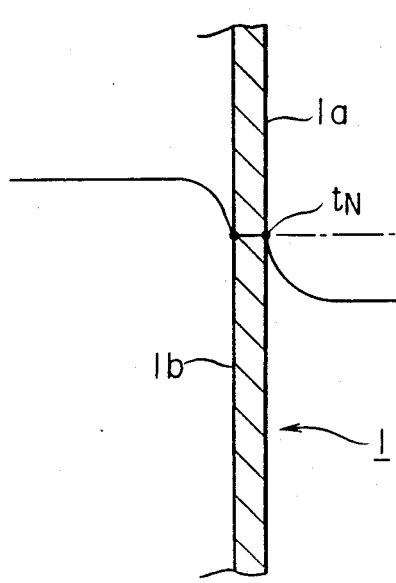
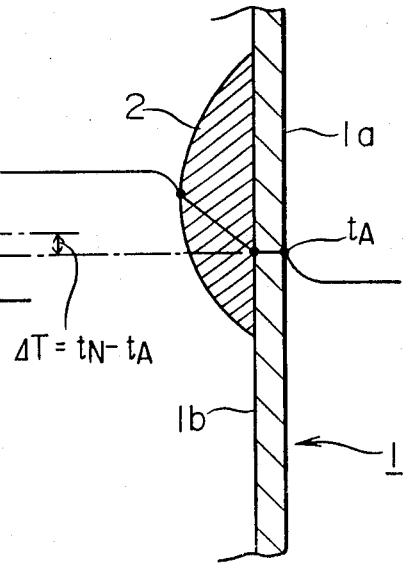
FIG. 9(A)  FIG. 9(B)

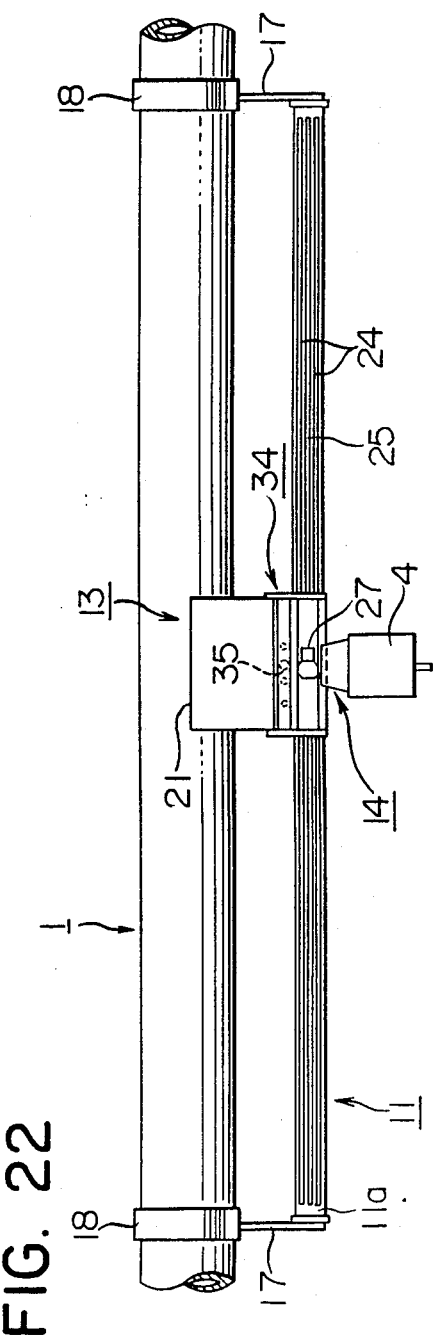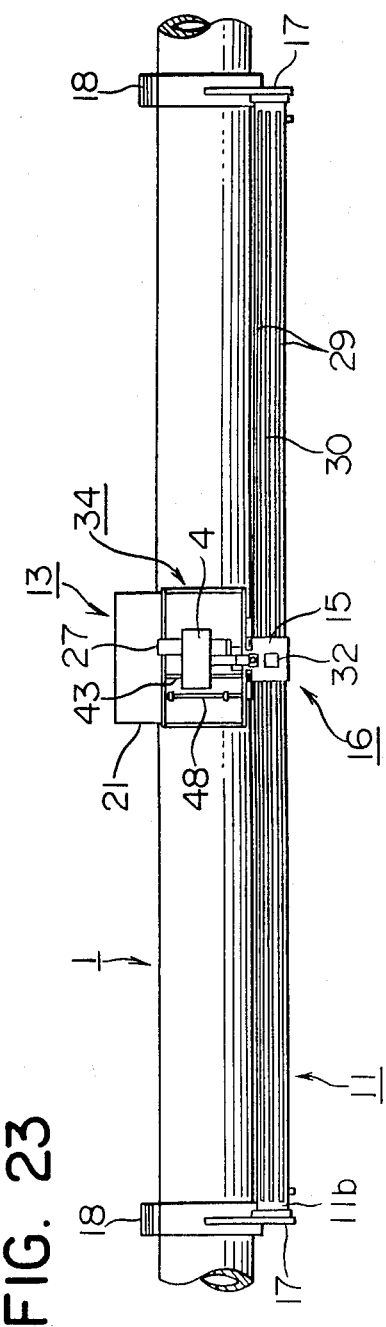

METHOD AND APPARATUS FOR DETECTING DEFECTIVE PORTION ON INNER SURFACE OF PIPE

FIELD OF THE INVENTION

The present invention relates to a method and an apparatus for detecting a defective portion existing on the inner surface of a pipe, the outer surface of which is exposed.

BACKGROUND OF THE INVENTION

On the inner surface of a pipe, the outer surface of which is exposed, installed on the ground for transporting, for example, a fluid such as a gas or a liquid, a defective portion such as those listed below may be present:

(1) an accumulation of foreign matters resulting from deposition of foreign matters such as rust and scale, and (2) a thinner portion caused by corrosion and the like.

Presence of an accumulation of foreign matters as mentioned above on the inner surface of a pipe causes such problems as impediment of smooth flow of the fluid in the pipe. Presence of a thinner portion as mentioned above on the inner surface of the pipe ultimately results, on the other hand, in such problems as production of a hole at the thinner portion. It is therefore necessary to promptly detect the above-mentioned defective portion on the inner surface of the pipe, and replace the pipe having the defective portion with a new one.

The following methods are known for detecting a defective portion on the inner surface of a pipe, the outer surface of which is exposed:

(1) Detecting method using radioactive rays:

This method comprises projecting radioactive rays such as X-ray or gamma-ray toward a pipe to be tested from the side of the outer surface thereof, measuring the amount of radioactive rays having passed through the pipe, and detecting a defective portion on the inner surface of the pipe by means of the amount of transmission of the radioactive rays.

(2) Detecting method using ultrasonic waves:

This method comprises transmitting ultrasonic waves toward a pipe to be tested from the side of the outer surface thereof, receiving reflected waves of the transmitted ultrasonic waves, measuring the time required up to receiving of the reflected waves of the transmitted ultrasonic waves, and detecting a defective portion on the inner surface of the pipe by means of the time required up to receiving of the reflected waves.

(3) Detecting method based on knocking:

This method comprises knocking a pipe to be tested from the side of the outer surface thereof with a hammer, for example, and detecting a defective portion on the inner surface of the pipe by means of the thus produced sound.

(b 4) Detecting method based on cutting:

This method comprises cutting out a pipe to be tested to permit an operator to directly observe the inner surface of the pipe, thereby detecting a defective portion on the inner surface of the pipe.

The detecting method using radioactive rays as mentioned in (1) above has the following problems (a) Detecting operation of a defective portion cannot be conducted unless the operator is qualified for handling radioactive rays. There is therefore a limitation in personnel.

(b) It is difficult to make a proper judgement on the result of detection, requiring high-level experience and technical knowledge.

(c) Detecting operation of a defective portion can be carried out only at a position closest to the outer surface of the pipe. When the pipe is installed at an elevated position apart from the ground, therefore, it is necessary to provide a scaffold for detecting operation.

(d) The range of a single run of detection is narrow. It thus requires much time and labor for detecting operation, leading to a low operating efficiency.

The detecting method using ultrasonic waves as mentioned in (2) above has the following problems (a) An error is often contained in the result of detection of a defective portion, thus preventing accurate detection.

(b) Detecting operation of a defective portion can be carried out only at a position in contact with the outer surface of the pipe. It is therefore difficult to conduct detecting operation when a high-temperature fluid flows through the pipe. When the pipe is installed at an elevated position apart from the ground, furthermore, it is necessary to provide a scaffold for detecting operation.

(c) The range of a single run of detection, being only a point, is very narrow. It thus requires much time and labor for detecting operation, leading to a low operating efficiency.

The detecting method based on knocking as mentioned in (3) above has the following problems (a) Determination of the presence of a defective portion requires high-level experience and technical knowledge, with furthermore much differences between individual operators, thus impairing accurate detection of the defective portion.

(b) Detecting operation of a defective portion can be carried out only at a position closest to the outer surface of the pipe. When the pipe is installed at an elevated position apart from the ground, therefore, it is necessary to provide a scaffold for detecting operation (c) Detecting operation requires much time and labor, resulting in a low operating efficiency.

(d) It is difficult to detect a small defective portion.

The detecting method based on cutting as mentioned in (b 4) above has the following problems (a) Use of the pipe must be interrupted for a while during cutting and detecting operations of a defective portion, and these cutting, detecting and restoring operations require much time and labor, resulting in a low operating efficiency.

(b) When the pipe is installed at an elevated position apart from the ground, it is necessary to provide a scaffold for detecting operation.

Under such circumstances, there is a strong demand for the development of a method and an apparatus which permit certain, easy and efficient detection of an accumulation of foreign matters or a thinner portion as a defective portion on the inner surface of a pipe, the outer surface of which is exposed, at a position apart from the pipe in a non-contact manner without the need for a special qualification, but a method and an apparatus provided with such properties have not as yet been proposed.

SUMMARY OF THE INVENTION

An object of the present invention is therefore to provide a method and an apparatus which permit certain, easy and efficient detection of an accumulation of foreign matters or a thinner portion as a defective portion on the inner surface of a pipe, the outer surface of which is exposed, at a position apart from the pipe in a non-contact manner without the need for a special qualification.

In accordance with one of the features of the present invention, there is provided a method for detecting a defective portion on the inner surface of a pipe, the outer surface of which is exposed, characterized by:

heating or cooling a pipe, the outer surface of which is exposed, from the side of the outer surface thereof so that a difference in temperature is produced between a portion of the outer surface of said pipe corresponding to a defective portion on the inner surface thereof and a portion of the outer surface of said pipe corresponding to a normal portion of the inner surface thereof; then shooting the outer surface of said pipe by means of a thermal imaging system while said difference in temperature still remains on the outer surface of said pipe to obtain a thermal image of said difference in temperature; and detecting said defective portion on the inner surface of said pipe by means of the thus obtained thermal image.

BRIEF DESCRIPTION OF THE DRAWINGS

FIG. 3 (B) is a descriptive view illustrating a temperature of a portion of the outer surface of a pipe corresponding to an accumulation of foreign matters on the inner surface of the pipe heated from the side of the outer surface thereof in accordance with the first embodiment of the method of the present invention as shown in FIG. 1;

FIG. 7 (B) is a graph illustrating the result of determination by simulation of changes in the surface temperature of steel sheets having a heat transfer rate $\alpha$ of 300 and having different thicknesses, after heating of the steel sheets for a certain period of time;

FIG. 7 (C) is a graph illustrating the result of determination by simulation of changes in the surface temperature of steel sheets having a heat transfer rate $\alpha$ of 1,000 and having different thicknesses, after heating of the steel sheets for a certain period of time;

FIG. 8 is a schematic descriptive side view illustrating a third embodiment of the method of the present invention;

FIG. 9 (A) is a descriptive view illustrating a temperature of a portion of the outer surface of a pipe corresponding to a normal portion of the inner surface of the pipe cooled from the side of the outer surface thereof in accordance with the third embodiment of the method of the present invention as shown in FIG. 8;

FIG. 9 (B) is a descriptive view illustrating a temperature of a portion of the outer surface of a pipe corresponding to an accumulation of foreign matters on the inner surface of the pipe cooled from the side of the outer surface thereof in accordance with the third embodiment of the method of the present invention as shown in FIG. 8;

FIG. 13 (B) is a descriptive view illustrating a temperature of a portion of the outer surface of a pipe corresponding to an accumulation of foreign matters on the inner surface of the pipe heated from the side of the inner surface thereof in accordance with the fifth embodiment of the method of the present invention as shown in FIG. 12;

FIG. 17 (B) is a descriptive view illustrating a temperature of a portion of the outer surface of a pipe corresponding to an accumulation of foreign matters on the inner surface of the pipe cooled from the side of the inner surface thereof in accordance with the seventh embodiment of the method of the present invention shown in FIG. 16;

FIG. 22 is a schematic plan view illustrating the embodiment of the apparatus of the present invention as shown in FIG. 21;

FIG. 23 is a schematic rear view illustrating the embodiment of the apparatus of the present invention as shown in FIG. 21;

DETAILED DESCRIPTION OF PREFERRED EMBODIMENTS

From the above-mentioned point of view, extensive studies were carried out to develop a method and an apparatus which permit certain, easy and efficient detection of an accumulation of foreign matters or a thinner portion as a defective portion existing on the inner surface of a pipe, the outer surface of which is exposed, at a position apart from the pipe in a non-contact manner without the need for a special qualification. As a result, the following finding was obtained:

For example, a pipe to be tested is heated or cooled for a certain period of time from the side of the outer surface thereof or the inner surface thereof. If there is an accumulation of foreign matters as a defective portion on the inner surface of the pipe, this accumulation of foreign matters has a lower thermal conductivity than that of a normal portion of the pipe. If there is a thinner portion as a defective portion on the inner surface of the pipe, on the other hand, this thinner portion has a smaller thermal capacity than that of a normal portion of the pipe. A difference in temperature is therefore produced between a portion of the outer surface of the pipe corresponding to the defective portion on the inner surface thereof, on the one hand, and a portion of the outer surface of the pipe corresponding to the normal portion of the inner surface of the pipe, on the other hand. By shooting the outer surface of the pipe while this difference in temperature still remains on the outer surface of the pipe by means of a thermal imaging system to obtain a thermal image of the above-mentioned difference in temperature, it is possible to detect the defective portion on the inner surface of the pipe by means of the thus obtained thermal image.

The present invention was developed on the basis of the aforementioned finding. Now, the method and the apparatus for detecting a defective portion on the inner surface of a pipe of the present invention are described with reference to drawings.

Figure 1:
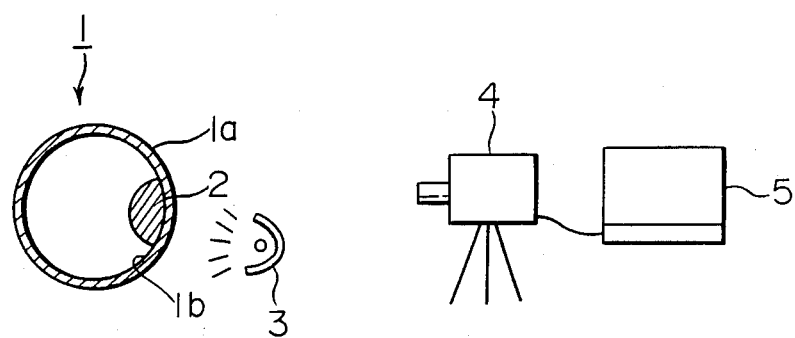
FIG. 1 is a schematic descriptive side view illustrating a first embodiment of the method of the present invention.
Figure 2:
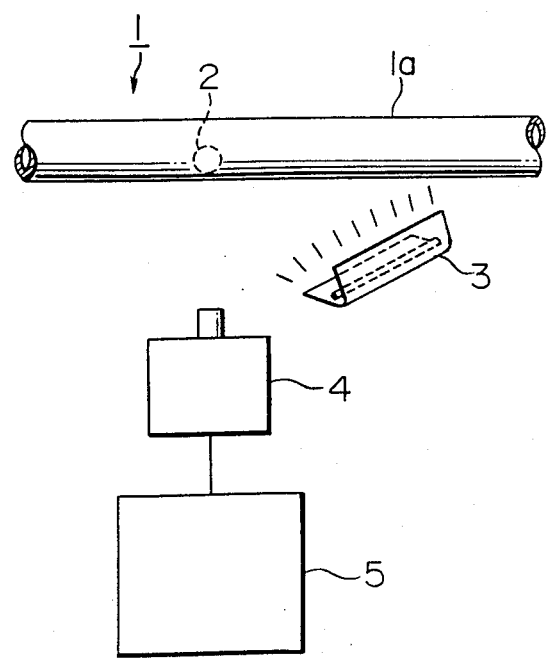
FIG. 2 is a schematic descriptive plan view illustrating the first embodiment of the method of the present invention as shown in FIG. 1.

FIG. 1 is a schematic descriptive side view illustrating a first embodiment of the method of the present invention, and FIG. 2 is a schematic descriptive plan view illustrating the first embodiment of the method of the present invention as shown in FIG. 1. As shown in FIGS. 1 and 2, in the first embodiment of the present invention, a pipe 1 to be tested, the outer surface 1a of which is exposed, is heated from the side of the outer surface 1a thereof by means Of a heating mechanism 3 so that a difference in temperature is produced between a portion of the outer surface 1a of the pipe 1 corresponding to an accumulation of foreign matters 2 such as rust and scale as a defective portion on the inner surface 1b thereof, on the one hand, and a portion of the outer surface 1a of the pipe 1 corresponding to a normal portion of the inner surface 1b thereof, on the other hand.

Figures 3A, 3B:
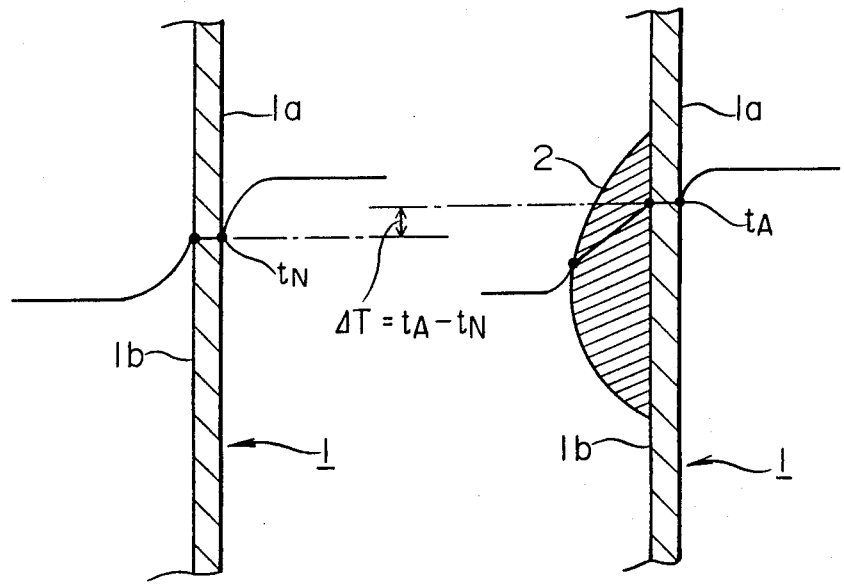
FIG. 3 (A) is a descriptive view illustrating a temperature of a portion of the outer surface of a pipe corresponding to a normal portion of the inner surface of the pipe heated from the side of the outer surface thereof in accordance with the first embodiment of the method of the present invention as shown in FIG. 1.

FIG. 3 (A) is a descriptive view illustrating a temperature of a portion of the outer surface 1a of the pipe 1 corresponding to a normal portion of the inner surface 1b of the pipe 1 heated from the side of the outer surface 1a thereof in accordance with the first embodiment of the method of the present invention; and FIG. 3 (B) is a descriptive view illustrating a temperature of a portion of the outer surface 1a of the pipe 1 corresponding to an accumulation of foreign matters 2 on the inner surface 1b of the pipe 1 heated as mentioned above. The accumulation of foreign matters 2 on the inner surface 1b of the pipe 1 has a thermal conductivity lower than that of the normal portion of the pipe 1. Accordingly, because of the presence of the accumulation of foreign matters 2 having a lower thermal conductivity, a temperature of the portion of the outer surface 1a of the pipe 1 corresponding to the accumulation of foreign matters 2 on the inner surface 1b thereof increases, by means of the above-mentioned heating, more rapidly than that of the portion of the outer surface 1a of the pipe 1 corresponding to the normal portion of the inner surface 1b thereof. As a result, as shown in FIGS. 3 (A) and 3 (B), the temperature $T_A$ of the portion of the outer surface 1a corresponding to the accumulation of foreign matters 2 on the inner surface 1b after heating for a certain period of time, is higher by $\Delta T$ than the temperature $t_N$ of the portion of the outer surface 1a corresponding to the normal portion of the inner surface 1b.

Figure 4:
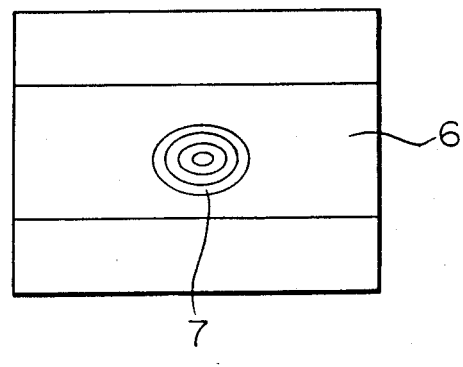
FIG. 4 is a descriptive view illustrating a typical thermal image shot in accordance with the first embodiment of the method of the present invention as shown in FIG. 1.

While the above-mentioned difference in temperature $\Delta T$ still remains on the outer surface 1a of the pipe 1, the outer surface 1a of the pipe 1 is shot by means of a thermal imaging system 4 to obtain a thermal image of the difference in temperature $\Delta T$, which has a portion showing a higher temperature, corresponding to the accumulation of foreign matters 2 on the inner surface 1b of the pipe 1. The thus obtained thermal image is displayed on a monitor TV screen 5. Therefore, it is possible to detect the accumulation of foreign matters 2 on the inner surface 1b of the pipe 1 by means of the above-mentioned thermal image. FIG. 4 is a descriptive view illustrating a typical thermal image shot in the manner as described above. As shown in FIG. 4, a thermal image 6 of the outer surface 1a of the pipe 1 has a portion 7 showing a higher temperature, which corresponds to the accumulation of foreign matters 2 on the inner surface 1b of the pipe 1, and which is indicated by colors predetermined for the respective ranges of temperature. More specifically, the inner portion indicating a relatively higher temperature of the above-mentioned portion 7 is different in color from the outer portion indicating a relatively lower temperature of the above-mentioned portion 7. It is therefore possible to detect a position, a shape and an approximate thickness of the accumulation of foreign matters 2 on the inner surface 1b of the pipe 1 by means of the portion 7 showing a higher temperature of the thermal image 6 as shown in FIG. 4.

The heating mechanism 3 capable of rapidly heating the pipe 1 within a short period of time, such as an infrared heater, should preferably be employed. When heating the pipe 1 from the side of the outer surface 1a thereof by means of the heating mechanism 3 and shooting the outer surface 1a of the pipe 1 by means of the thermal imaging system 4, it is necessary to heat the pipe 1 from the side of the outer surface 1a thereof for such a period of time as to produce the above-mentioned difference in temperature $\Delta T$ between the portion of the outer surface 1a of the pipe 1 corresponding to the accumulation of foreign matters 2 on the inner surface 1b thereof, on the one hand, and the portion of the outer surface 1a of the pipe 1 corresponding to the normal portion of the inner surface 1b thereof, on the other hand, and to shoot the outer surface 1a of the pipe 1 by means of the thermal imaging system 4 while the above-mentioned difference in temperature $\Delta T$ still remains on the outer surface 1a of the pipe 1. The difference in temperature $\Delta T$ becomes almost null if the period of time for heating and for shooting after the end of heating exceeds a certain duration, thus making it impossible to detect the accumulation of foreign matters 2 on the inner surface 1b of the pipe 1. The above-mentioned heating time should therefore be appropriately set with reference to the thickness of the pipe 1, the range of heating of the outer surface 1a of the pipe 1, the state of occurrence of the accumulation of foreign matters 2 and the performance of the thermal imaging system 4.

It is possible to emphatically produce the abovementioned difference in temperature $\Delta T$ between the portion of the outer surface 1a of the pipe 1 corresponding to the accumulation of foreign matters 2 on the inner surface 1b thereof, on the one hand, and the portion of the outer surface 1a of the pipe 1 corresponding to the normal portion of the inner surface 1b thereof, on the other hand, by cooling the pipe 1 from the side of the inner surface 1b thereof prior to the heating of the pipe 1 from the side of the outer surface 1a thereof in accordance with the first embodiment of the method of the present invention as described above. By shooting the outer surface 1a of the pipe 1 by means of the thermal imaging system 4 while the thus emphatically produced difference in temperature $\Delta T$ still remains on the outer surface 1a of the pipe 1, therefore, it is possible to detect more accurately the accumulation of foreign matters 2 on the inner surface 1b of the pipe 1 in the form of a further clearer thermal image representing the difference in temperature $\Delta T$.

Figure 5:
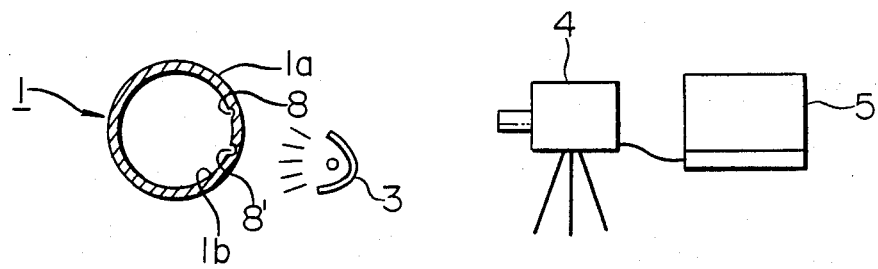
FIG. 5 is a schematic descriptive side view illustrating a second embodiment of the method of the present invention.

FIG. 5 is a schematic descriptive side view illustrating a second embodiment of the method of the present invention. As shown in FIG. 5, in the second embodiment of the method of the present invention, a pipe 1 to be tested, the outer surface of which is exposed, is heated from the side of the outer surface 1a thereof by means of a heating mechanism 3 so that a difference in temperature is produced between portions of the outer surface 1a of the pipe 1 corresponding to thinner portions 8 and 8' as defective portions on the inner surface 1b thereof, on the one hand, and a portion of the outer surface 1a of the pipe 1 corresponding to a normal portion of the inner surface 1b thereof, on the other hand.

Figure 6:
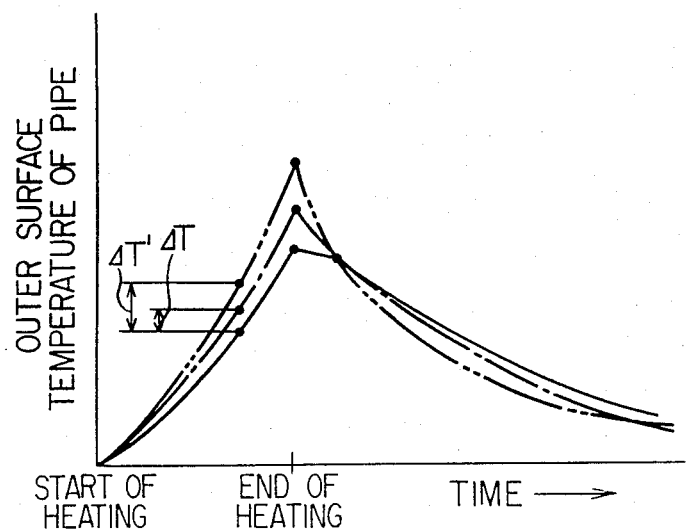
FIG. 6 is a graph illustrating changes in temperature, which are caused by heating a pipe from the side of the outer surface thereof in accordance with the second embodiment of the method of the present invention as shown in FIG. 5, at a portion of the outer surface of the pipe corresponding to a normal portion of the inner surface thereof, and at a portion of the outer surface of the pipe corresponding to a thinner portion on the inner surface thereof.

FIG. 6 is a graph illustrating changes in temperature, which are caused by heating a pipe 1 from the side of the outer surface 1a thereof in accordance with the second embodiment of the method of the present invention, at a portion of the outer surface 1a of the pipe 1 corresponding to a normal portion of the inner surface 1b thereof, and at portions of the outer surface 1a of the pipe 1 corresponding to thinner portions 8 and 8' on the inner surface 1b thereof. In FIG. 6, the solid line represents changes in temperature at a portion of the outer surface 1a corresponding to a normal portion of the inner surface 1b; the one-point chain line represents changes in temperature at a portion of the outer surface 1a corresponding to a shallower thinner portion 8 on the inner surface 1b; and the two-point chain line represents changes in temperature at a portion of the outer surface 1a corresponding to a deeper thinner portion 8' on the inner surface 1b. The thinner portions 8 and 8' on the inner surface 1b of the pipe 1 have a thermal capacity smaller than that of the normal portion of the pipe 1. Accordingly, a temperature of the portions of the outer surface 1a of the pipe 1 corresponding to the thinner portions 8 and 8' on the inner surface 1b thereof increases, by means of the above-mentioned heating, more rapidly than that of the portion of the outer surface 1a of the pipe 1 corresponding to the normal portion of the inner surface 1b thereof. As a result, as shown in FIG. 6, during the period of time of from start to end of heating and for a certain period of time after the end of heating, the temperature of the portion of the outer surface 1a corresponding to the shallower thinner portion 8 on the Inner surface 1b, as represented by the one-point chain line, is higher by $\Delta T$ than the temperature of the portion of the outer surface 1a corresponding to the normal portion of the inner surface 1b, as represented by the solid line, and the temperature of the portion of the outer surface 1a corresponding to the deeper thinner portion 8' on the inner surface 1b, as represented by the two-point chain line, is higher by $\Delta T'$ than the temperature of the portion of the outer surface 1a corresponding to the normal portion of the inner surface 1b, as represented by the solid line. The difference in temperature $\Delta T'$ of the deeper thinner portion 8' from the normal portion is larger than the difference in temperature $\Delta T$ of the shallower thinner portion 8 from the normal portion.

While the above-mentioned differences in temperature $\Delta T$ and $\Delta T'$ still remain on the outer surface 1a of the pipe 1, the outer surface 1a of the pipe 1 is shot by means of a thermal imaging system 4 to obtain a thermal image of the differences in temperature $\Delta T$ and $\Delta T'$, which has portions showing a higher temperature, corresponding to the thinner portions 8 and 8' on the inner surface 1b of the pipe 1. The thus obtained thermal image is displayed on a monitor TV screen 5. Therefore, it is possible to detect the shallower thinner portion 8 and the deeper thinner portion 8' on the inner surface 1b of the pipe 1 by means of the above-mentioned thermal image. More specifically, it is possible to detect a position, a shape and an approximate depth of the thinner portions 8 and 8' on the inner surface 1b of the pipe 1 by means of the portion showing a higher temperature of the above mentioned thermal image.

When heating the pipe 1 from the side of the outer surface 1a thereof by means of the heating mechanism 3 and shooting the outer surface 1a of the pipe 1 by means of the thermal imaging system 4, it is necessary to heat the pipe 1 from the side of the outer surface 1a thereof for such a period of time as to produce the above-mentioned differences in temperature $\Delta T$ and $\Delta T'$ between the portions of the outer surface 1a of the pipe 1 corresponding to the thinner portions 8 and 8' on the inner surface 1b thereof, on the one hand, and the portion of the outer surface 1a of the pipe 1 corresponding to the normal portion of the inner surface 1b thereof, on the other hand, and to shoot the outer surface 1a of the pipe 1 by means of the thermal imaging system 4 while the abovementioned differences in temperature $\Delta T$ and $\Delta T'$ still remain on the outer surface 1a of the pipe 1.

Furthermore, when cold water is passed through the pipe 1, for example, to cool the pipe 1 from the side of the inner surface 1b thereof, after the end of heating of the pipe 1 from the side of the outer surface 1a thereof, the temperature of the portions of the outer surface 1a corresponding to the thinner portions 8 and 8' becomes lower than that of the portion of the outer surface 1a corresponding to the normal portion of the inner surface 1b in the middle of the course of decrease of the temperature of the outer surface 1a to the original temperature thereof, as shown in FIG. 6, thus producing differences in temperature between these portions of the outer surface 1a.

While the above-mentioned differences in temperature still remain on the outer surface 1a of the pipe 1, the outer surface 1a of the pipe 1 is shot by means of the thermal imaging system 4 to obtain a thermal image of the differences in temperature, which has portions showing a lower temperature, corresponding to the thinner portions 8 and 8' on the inner surface 1b of the pipe 1. The thus obtained thermal image is displayed on the monitor TV screen 5. Therefore, it is possible to detect the thinner portions 8 and 8' on the inner surface 1b of the pipe 1 by means of the above-mentioned thermal image.

Figure 7:
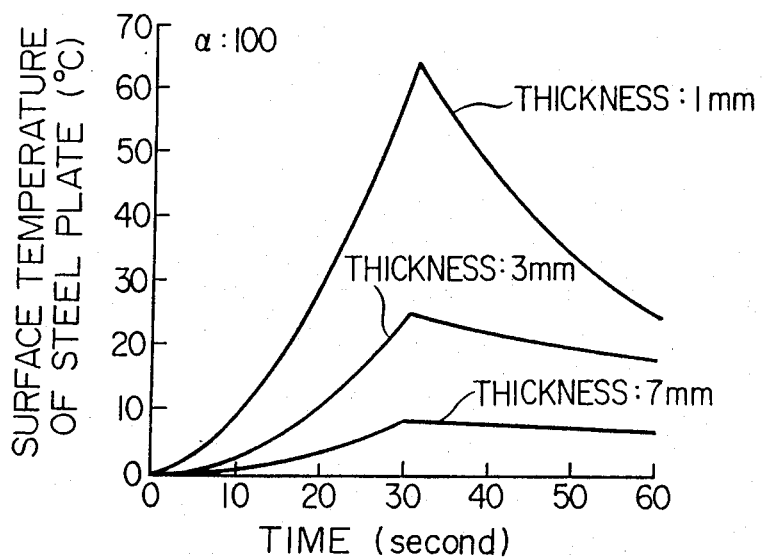
FIG. 7 (A) is a graph illustrating the result of determination by simulation of changes in the surface temperature of steel sheets having a heat transfer rate $\alpha$ of 100 and having different thicknesses, after heating of the steel sheets for a certain period of time.
Figure 7:
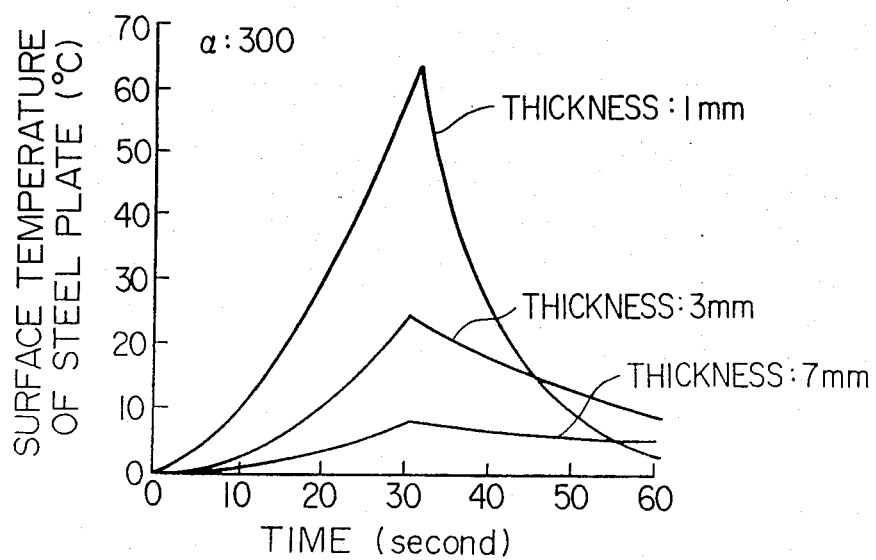
Figure 7C:
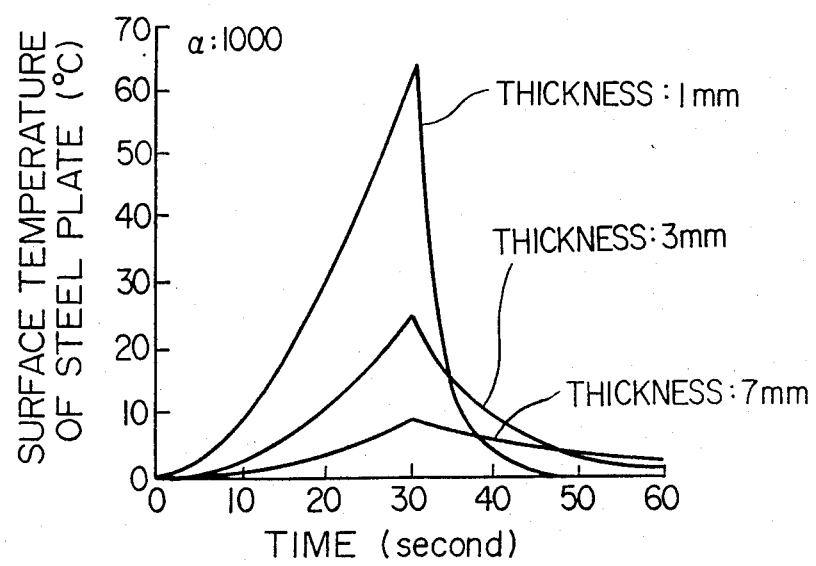

FIG. 7 (A) is a graph illustrating the result of determination by simulation of changes in the surface temperature of steel sheets having a heat transfer rate $\alpha$ of 100 and having thicknesses of 1 mm, 3 mm and 7 mm, respectively, after heating of the steel sheets for 30 seconds and then leaving to cool same for 30 seconds; FIG. 7 (B) is a graph illustrating the result of determination by simulation of changes in the surface temperature of steel sheets under the same conditions as above except for a heat transfer rate $\alpha$ of 300, after heating of the steel sheets and then leaving to cool same; and FIG. 7 (C) is a graph illustrating the result of determination by simulation of changes in the surface temperature of steel sheets under the same conditions as above except for a heat transfer rate $\alpha$ of 1,000, after heating of the steel sheets and then leaving to cool same. The simulation was performed on the assumption of the absence of heat radiation from the surfaces of the steel sheets during heating, a uniform temperature distribution in the thickness direction of the steel sheets, and the absence of heat transfer in the longitudinal direction of the steel sheets.

As is clear from FIGS. 7 (A), 7 (B) and 7 (C), apart from some minor differences in extent depending on the magnitude of heat transfer rate $\alpha$, a thinner steel sheet shows a higher rate of temperature increase during heating and a higher rate of temperature decrease during cooling. This suggests that there is produced a change in the temperature of the portion of the outer surface of the pipe corresponding to the thinner portion on the inner surface thereof according to the presence of the thinner portion on the inner surface of the pipe and the depth of the thinner portion.

It is possible to emphatically produce the abovementioned differences in temperature $\Delta T$ and $\Delta T'$ between the portions of the outer surface 1a of the pipe 1 corresponding to the thinner portions 8 and 8' on the inner surface 1b thereof, on the one hand, and the portion of the outer surface 1a of the pipe 1 corresponding to the normal portion of the inner surface 1b thereof, on the other hand, by cooling the pipe 1 from the side of the inner surface 1b thereof prior to the heating of the pipe 1 from the side of the outer surface 1a thereof in accordance with the second embodiment of the method of the present invention as described above. By shooting the outer surface 1a of the pipe 1 by means of the thermal imaging system 4 while the thus emphatically produced differences in temperature $\Delta T$ and $\Delta T'$ still remain on the outer surface 1a of the pipe 1, therefore, it is possible to detect more accurately the thinner portions 8 and 8' on the inner surface 1b of the pipe 1 in the form of a further clearer thermal image representing the differences in temperature $\Delta T$ and $\Delta T'$.

FIG. 8 is a schematic descriptive side view illustrating a third embodiment of the method of the present invention. As shown in FIG. 8, in the third embodiment of the method of the present invention, a pipe 1 to be tested, the outer surface 1a of which is exposed, is cooled from the side of the outer surface 1a thereof by means of a cooling mechanism 9 so that a difference in temperature is produced between a portion of the outer surface 1a of the pipe 1 corresponding to an accumulation of foreign matters 2 as a defective portion on the inner surface 1b thereof, on the one hand, and a portion of the outer surface 1a of the pipe 1 corresponding to a normal portion of the inner surface 1b thereof, on the other hand.

FIG. 9 (A) is a descriptive view illustrating a temperature of a portion of the outer surface 1a of the pipe 1 corresponding to a normal portion of the inner surface 1b of the pipe 1 cooled from the side of the outer surface 1a thereof in accordance with the third embodiment of the method of the present invention; and FIG. 9 (B) is a descriptive view illustrating a temperature of a portion of the outer surface 1a of the pipe 1 corresponding to an accumulation of foreign matters 2 on the inner surface 1b of the pipe cooled as mentioned above. As described above, the accumulation of foreign matters 2 on the inner surface 1b of the pipe 1 has a thermal conductivity lower than that of the normal portion of the pipe 1. Accordingly, because of the presence of the accumulation of foreign matters 2 having a lower thermal conductivity, a temperature of the portion of the outer surface 1a of the pipe corresponding to the accumulation of foreign matters 2 on the inner surface 1b thereof decreases, by means of the above-mentioned cooling, more rapidly than that of the portion of the outer surface 1a of the pipe 1 corresponding to the normal portion of the inner surface 1b thereof. As a result, as shown in FIGS. 9 (A) and 9 (B), the temperature $T_A$ of the portion of the outer surface 1a corresponding to the accumulation of foreign matters 2 on the inner surface 1b, after cooling for a certain period of time, is lower by $\Delta T$ than the temperature $t_N$ of the portion of the outer surface 1a corresponding to the normal portion of the inner surface 1b.

While the above-mentioned difference in temperature $\Delta T$ still remains on the outer surface 1a of the pipe 1, the outer surface 1a of the pipe 1 is shot by means of a thermal imaging system 4 to obtain a thermal image of the difference in temperature $\Delta T$, which has a portion showing a lower temperature, corresponding to the accumulation of foreign matters 2 on the inner surface 1b of the pipe 1. The thus obtained thermal image is displayed on a monitor TV screen 5. Therefore, it is possible to detect the accumulation of foreign matters 2 on the inner surface 1b of the pipe 1 by means of the above-mentioned thermal image. More specifically, it is possible to detect a position, a shape and an approximate thickness of the accumulation of foreign matters 2 on the inner surface 1b of the pipe 1 by means of the portion showing a lower temperature of the above-mentioned thermal image.

Cooling of the pipe 1 from the side of the outer surface 1a thereof is accomplished by spraying a cooling medium onto the outer surface 1a of the pipe 1 by means of a cooling mechanism 9. An applicable cooling medium includes, in addition to water and air, a freon-based liquefied gas such as trifluorotrichlorethane and a low-boiling-point liquid such as acetone, ether or alcohol. When a liquefied gas or a low-boiling-point liquid as the cooling medium as described above is sprayed onto the outer surface 1a of the pipe 1, the sprayed liquefied gas or low-boiling-point liquid rapidly evaporates and takes evaporation heat. The outer surface 1a of the pipe 1 is therefore rapidly cooled, thus permitting rapid detection of the accumulation of foreign matters 2 on the inner surface 1a of the pipe 1 by means of the thermal imaging system 4.

It is possible to emphatically produce the above-mentioned difference in temperature $\Delta T$ between the portion of the outer surface 1a of the pipe 1 corresponding to the accumulation of foreign matters 2 on the inner surface 1b thereof, on the one hand, and the portion of the outer surface 1a of the pipe 1 corresponding to the normal portion of the inner surface 1b thereof, on the other hand, by heating the pipe 1 from the side of the inner surface 1b thereof prior to the cooling of the pipe 1 from the side of the outer surface 1a thereof in accordance with the third embodiment of the method of the present invention as described above. By shooting the outer surface 1a of the pipe 1 by means of the thermal imaging system 4 while the thus emphatically produced difference in temperature $\Delta T$ still remains on the outer surface 1a of the pipe 1, therefore, it is possible to detect more accurately the accumulation of foreign matters 2 on the inner surface 1b of the pipe 1 in the form of a further clearer thermal image representing the difference in temperature $\Delta T$.

Figure 10:
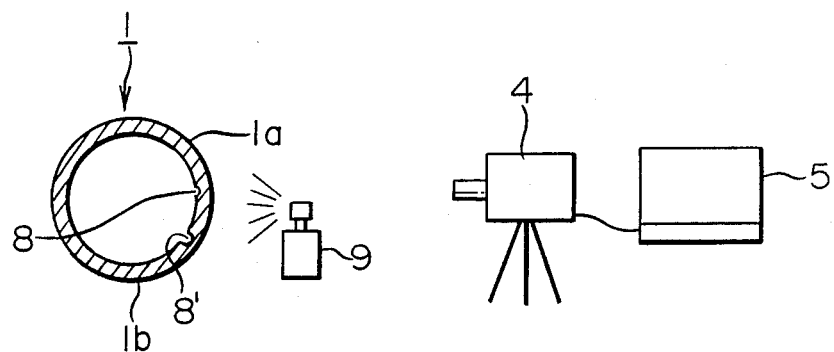
FIG. 10 is a schematic descriptive side view illustrating a fourth embodiment of the method of the present invention.

FIG. 10 is a schematic descriptive side view illustrating a fourth embodiment of the method of the present invention. As shown in FIG. 10, in the fourth embodiment of the method of the present invention, a pipe 1 to be tested, the outer surface 1a of which is exposed, is cooled from the side of the outer surface 1a thereof by means of a cooling mechanism 9 so that a difference in temperature is produced between portions of the outer surface 1a of the pipe 1 corresponding to thinner portions 8 and 8' as defective portions on the inner surface 1b thereof, on the one hand, and a portion of the outer surface 1a of the pipe 1 corresponding to a normal portion of the inner surface 1b thereof, on the other hand.

Figure 11:
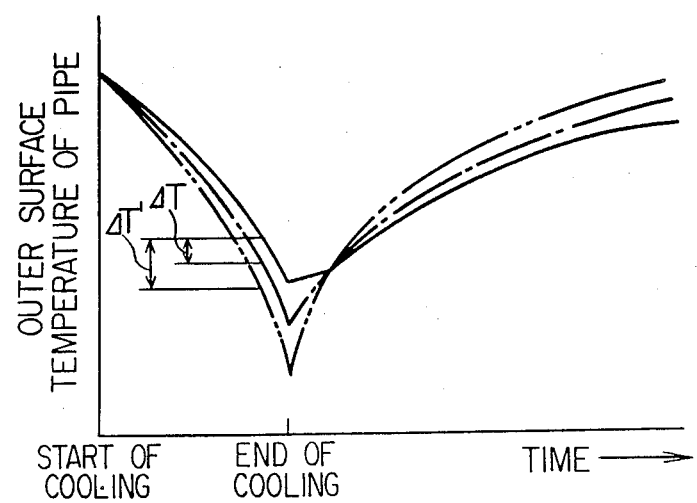
FIG. 11 is a graph illustrating changes in temperature, which are caused by cooling a pipe from the side of the outer surface thereof in accordance with the fourth embodiment of the method of the present invention as shown in FIG. 10, at a portion of the outer surface of the pipe corresponding to a normal portion of the inner surface thereof, and at a portion of the outer surface of the pipe corresponding to a thinner portion on the inner surface thereof.

FIG. 11 is a graph illustrating changes in temperature, which are caused by cooling a pipe 1 from the side of the outer surface 1a thereof in accordance with the fourth embodiment of the method of the present invention, at a portion of the outer surface 1a of the pipe 1 corresponding to a normal portion of the inner surface 1b thereof, and at portions of the outer surface 1a of the pipe 1 corresponding to thinner portions 8 and 8' on the inner surface 1b thereof. As described above, the thinner portions 8 and 8' on the inner surface 1b of the pipe 1 have a thermal capacity smaller than that of the normal portion of the pipe 1. Accordingly, a temperature of the portions of the outer surface 1a of the pipe 1 corresponding to the thinner portions 8 and 8' on the inner surface 1b thereof decreases, by means of the above-mentioned cooling, more rapidly than that of the portion of the outer surface 1a corresponding to the normal portion of the inner surface 1b of the pipe 1. As a result, as shown in FIG. 11, during the period of time from start to end of cooling and for a certain period of time after the end of cooling, the temperature of the portion of the outer surface 1a corresponding to a shallower thinner portion 8 on the inner surface 1b, as represented by the one-point chain line, is lower by $\Delta T$ than the temperature of the portion of the outer surface 1a corresponding to the normal portion of the inner surface 1b, as represented by the solid line, and the temperature of the portion of the outer surface 1a corresponding to a deeper thinner portion 8' on the inner surface 1b, as represented by the two-point chain line, is lower by $\Delta T'$ than the temperature of the portion of the outer surface 1a corresponding to the normal portion of the inner surface 1b, as represented by the solid line. The difference in temperature $\Delta T'$ of the deeper thinner portion 8' from the normal portion is larger than the difference in temperature $\Delta T$ of the shallower thinner portion 8 from the normal portion.

While the above-mentioned differences in temperature $\Delta T$ and $\Delta T'$ still remain on the outer surface 1a of the pipe 1, the outer surface 1a of the pipe 1 is shot by means of a thermal imaging system 4 to obtain a thermal image of the differences in temperature $\Delta T$ and $\Delta T'$, which has portions showing a lower temperature, corresponding to the thinner portions 8 and 8' on the inner surface 1b of the pipe 1. The thus obtained thermal image is displayed on a monitor TV screen 5. Therefore, it is possible to detect the shallower thinner portion 8 and the deeper thinner portion 8' on the inner surface 1b of the pipe 1 by means of the above-mentioned thermal image. More specifically, it is possible to detect a position, a shape and an approximate depth of the thinner portions 8 and 8' on the inner surface 1b of the pipe 1 by means of the portion showing a lower temperature of the above mentioned thermal image.

Furthermore, when hot water is passed through the pipe 1, for example, to heat the pipe 1 from the side of the inner surface 1b thereof, after the end of cooling of the pipe 1 from the side of the outer surface 1a thereof, the temperature of the portions of the outer surface 1a corresponding to the thinner portions 8 and 8′ becomes higher than that of the portion of the outer surface 1a corresponding to the normal portion of the inner surface 1b in the middle of the course of increase of the temperature of the outer surface 1b to the original temperature thereof, as shown in FIG. 11, thus producing differences in temperature between these portions of the outer surface 1a.

While the above-mentioned differences in temperature still remain on the outer surface 1a of the pipe 1, the outer surface 1a of the pipe 1 is shot by means of the thermal imaging system 4 to obtain a thermal image of the differences in temperature, which has portions showing a higher temperature, corresponding to the thinner portions 8 and 8′ on the inner surface 1b of the pipe 1. The thus obtained thermal image is displayed on the monitor TV screen 5. Therefore, it is possible to detect the thinner portions 8 and 8′ on the inner surface 1b of the pipe 1 by means of the above-mentioned thermal image.

It is possible to emphatically produce the above-mentioned differences in temperature $\Delta T$ and $\Delta T'$ between the portions of the outer surface 1a of the pipe 1 corresponding to the thinner portions 8 and 8′ on the inner surface 1b thereof, on the one hand, and the portion of the outer surface 1a of the pipe 1 corresponding to the normal portion of the inner surface 1b thereof, on the other hand, by heating the pipe 1 from the side of the inner surface 1b thereof prior to the cooling of the pipe 1 from the side of the outer surface 1a thereof in accordance with the fourth embodiment of the method of the present invention as described above. By shooting the outer surface 1a of the pipe 1 by means of the thermal imaging system 4 while the thus emphatically produced differences in temperature $\Delta T$ and $\Delta T'$ still remain on the outer surface 1a of the pipe 1, therefore, it is possible to detect more accurately the thinner portions 8 and 8′ on the inner surface 1b of the pipe 1 in the form of a further clearer thermal image representing the differences in temperature $\Delta T$ and $\Delta T'$.

Figure 12:
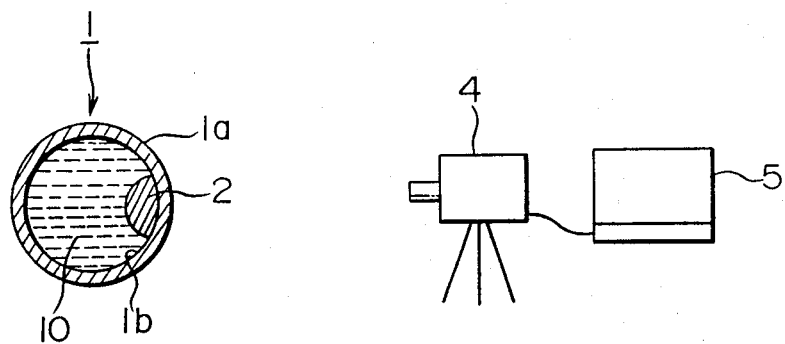
FIG. 12 is a schematic descriptive side view illustrating a fifth embodiment of the method of the present invention.

FIG. 12 is a schematic descriptive side view illustrating a fifth embodiment of the method of the present invention. As shown in FIG. 12, in the fifth embodiment of the present invention, a pipe 1 to be tested, the outer surface 1a of which is exposed, is heated from the side of the inner surface 1b thereof so that a difference in temperature is produced between a portion of the outer surface 1a of the pipe 1 corresponding to an accumulation of foreign matters 2 as a defective portion on the inner surface 1b thereof, on the one hand, and a portion of the outer surface 1a of the pipe 1 corresponding to a normal portion of the inner surface 1b thereof, on the other hand.

Figures 13A, 13B:
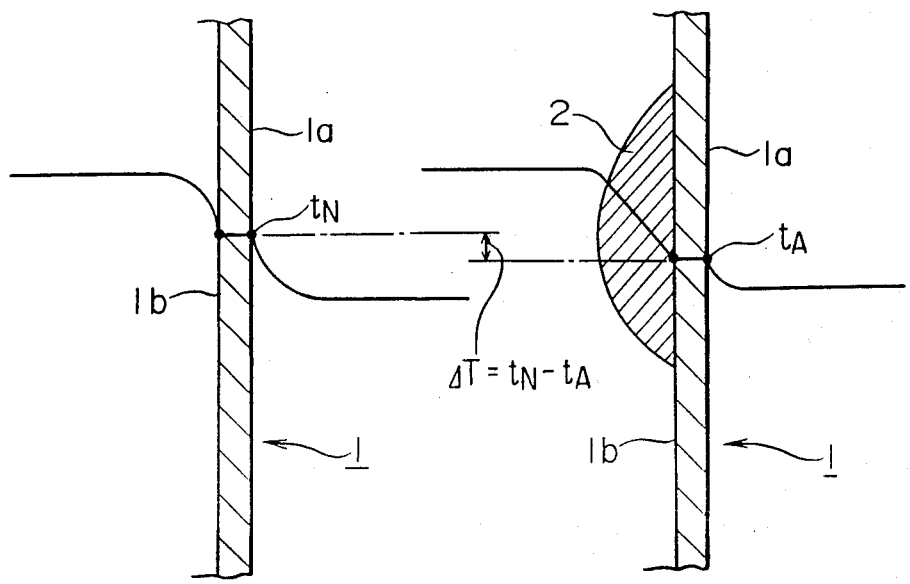
FIG. 13 (A) is a descriptive view illustrating a temperature of a portion of the outer surface of a pipe corresponding to a normal portion of the inner surface of the pipe heated from the side of the inner surface thereof in accordance with the fifth embodiment of the method of the present invention as shown in FIG. 12.

FIG. 13 (A) is a descriptive view illustrating a temperature of a portion of the outer surface 1a of the pipe 1 corresponding to a normal portion of the inner surface 1b of the pipe 1 heated from the side of the inner surface 1b thereof in accordance with the fifth embodiment of the method of the present invention; and FIG. 13 (B) is a descriptive view illustrating a temperature of a portion of the outer surface 1a of the pipe 1 corresponding to an accumulation of foreign matters 2 on the inner surface 1b of the pipe 1 heated as mentioned above. As described above, the accumulation of foreign matters 2 on the inner surface 1b of the pipe 1 has a thermal conductivity lower than that of the normal portion of the pipe 1. Accordingly, because of the presence of the accumulation of foreign matters 2 having a lower thermal conductivity, a temperature of the portion of the outer surface 1a of the pipe 1 corresponding to the accumulation of foreign matters 2 on the inner surface 1b thereof increases, by means of the above-mentioned heating, more slowly than that of the portion of the outer surface 1a of the pipe 1 corresponding to the normal portion of the inner surface 1b thereof. As a result, as shown in FIGS. 13 (A) and 13 (B), the temperature $T_A$ of the portion of the outer surface 1a corresponding to the accumulation of foreign matters 2 after heating for a certain period of time, is lower by $\Delta T$ than the temperature $t_N$ of the portion of the outer surface 1a corresponding to the normal portion of the inner surface 1b.

While the above-mentioned difference in temperature $\Delta T$ still remains on the outer surface 1a of the pipe 1, the outer surface 1a of the pipe 1 is shot by means of a thermal imaging system 4 to obtain a thermal image of the difference in temperature $\Delta T$, which has a portion showing a lower temperature, corresponding to the accumulation of foreign matters 2 on the inner surface 1b of the pipe 1. The thus obtained thermal image is displayed on a monitor TV screen 5. Therefore, it is possible to detect the accumulation of foreign matters 2 on the inner surface 1b of the pipe 1 by means of the above-mentioned thermal image. More specifically, it is possible to detect a position, a shape and an approximate thickness of the accumulation of foreign matters 2 on the inner surface 1b of the pipe 1 by means of the portion showing a lower temperature of the above-mentioned thermal image.

Heating of the pipe 1 from the side of the inner surface 1b thereof is accomplished by passing a high-temperature fluid 10 such as a high-temperature liquid or gas through the pipe 1 or by inserting a heating mechanism (not shown) into the pipe 1. When a high-temperature fluid 10 flows through the pipe 1, the pipe 1 may be heated by the use of the flowing high-temperature fluid 10.

It is possible to emphatically produce the above-mentioned difference in temperature $\Delta T$ between the portion of the outer surface 1a of the pipe 1 corresponding to the accumulation of foreign matters 2 on the inner surface 1b thereof, on the one hand, and the portion of the outer surface 1a of the pipe 1 corresponding to the normal portion of the inner surface 1b thereof, on the other hand, by cooling the pipe 1 from the side of the outer surface 1a thereof prior to the heating of the pipe 1 from the side of the inner surface 1b thereof in accordance with the fifth embodiment of the method of the present invention as described above. By shooting the outer surface 1a of the pipe 1 by means of the thermal imaging system 4 while the thus emphatically produced difference in temperature $\Delta T$ still remains on the outer surface 1a of the pipe 1, therefore, it is possible to detect more accurately the accumulation of foreign matters 2 on the inner surface 1b of the pipe 1 in the form of a further clearer thermal image representing the difference in temperature $\Delta T$.

Figure 14:
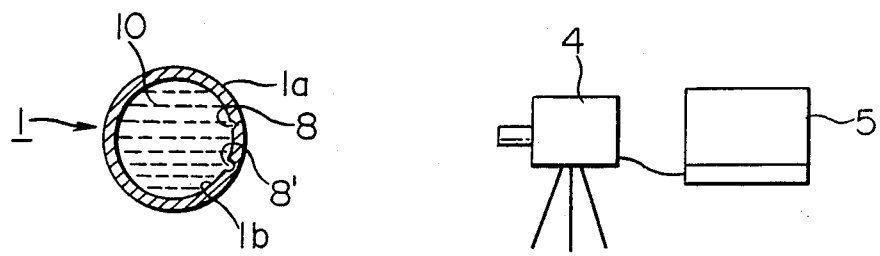
FIG. 14 is a schematic descriptive side view illustrating a sixth embodiment of the method of the present invention.

FIG. 14 is a schematic descriptive side view illustrating a sixth embodiment of the method of the present invention. As shown in FIG. 14, in the sixth embodiment of the present invention, a pipe 1 to be tested, the outer surface 1a of which is exposed, is heated from the side of the inner surface 1b thereof so that a difference in temperature is produced between portions of the outer surface 1a of the pipe 1 corresponding to thinner portions 8 and 8' as defective portions on the inner surface 1b thereof, on the one hand, and a portion of the outer surface 1a of the pipe 1 corresponding to a normal portion of the inner surface 1b thereof, on the other hand.

Figure 15:
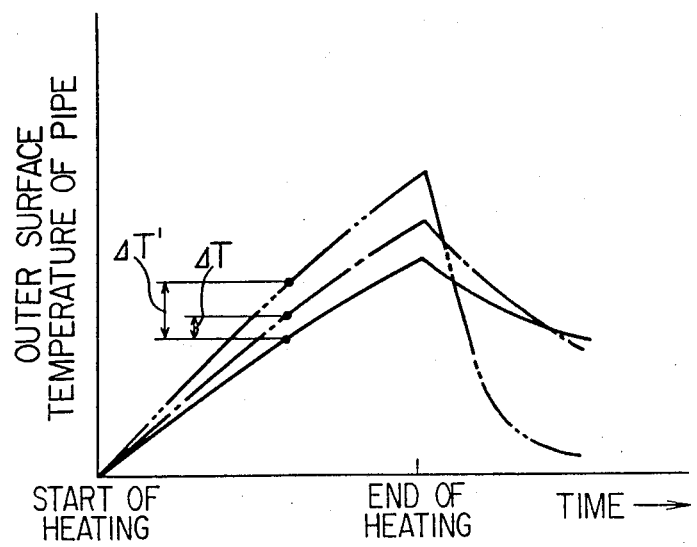
FIG. 15 is a graph illustrating changes in temperature, which are caused by heating a pipe from the side of the inner surface thereof in accordance with the sixth embodiment of the method of the present invention as shown in FIG. 14, at a portion of the outer surface of the pipe corresponding to a normal portion of the inner surface thereof, and at a portion of the outer surface of the pipe corresponding to a thinner portion on the inner surface thereof.

FIG. 15 is a graph illustrating changes in temperature, which are caused by heating a pipe from the side of the inner surface 1b thereof in accordance with the sixth embodiment of the method of the present invention, at a portion of the outer surface 1a of the pipe 1 corresponding to a normal portion of the inner surface 1b thereof, and at a portion of the outer surface 1a of the pipe 1 corresponding to thinner portions 8 and 8' on the inner surface 1b thereof. As described above, the thinner portions 8 and 8' on the inner surface 1b of the pipe 1 have a thermal capacity smaller than that of the normal portion of the pipe 1. Accordingly, a temperature of the portions of the outer surface 1a of the pipe 1 corresponding to the thinner portions 8 and 8' on the inner surface 1b thereof increases, by means of the abovementioned heating, more rapidly than that of the portion of the outer surface 1a corresponding to the normal portion of the inner surface 1b of the pipe 1. As a result as shown in FIG. 15, during the period of time of from start to end of heating and for a certain period of time after the end of heating, the temperature of the portion of the outer surface 1a corresponding to the shallower thinner portion 8 on the inner surface 1b, as represented by the one-point chain line, is higher by $\Delta T$ than the temperature of the portion of the outer surface 1a corresponding to the normal portion of the inner surface 1b, as represented by the solid line, and the temperature of the portion of the outer surface 1a corresponding to the deeper thinner portion 8' on the inner surface 1b, as represented by the two-point chain line, is higher by $\Delta T'$ than the temperature of the portion of the outer surface 1a corresponding to the normal portion of the inner surface 1b, as represented by the solid line. The difference in temperature $\Delta T'$ of the deeper thinner portion 8' from the normal portion is larger than the difference in temperature $\Delta T$ of the shallower thinner portion 8 from the normal portion.

While the above-mentioned differences in temperature $\Delta T$ and $\Delta T'$ still remain on the outer surface 1a of the pipe 1, the outer surface 1a of the pipe 1 is shot by means of a thermal imaging system 4 to obtain a thermal image of the differences in temperature $\Delta T$ and $\Delta T'$, which has portions showing a higher temperature, corresponding to the thinner portions 8 and 8' on the inner surface 1b of the pie 1. The thus obtained thermal image is displayed on a monitor TV screen 5. Therefore, it is possible to detect the shallower thinner portion 8 and the deeper thinner portion 8' on the inner surface 1b of the pipe 1 by means of the above-mentioned thermal image. More specifically, it is possible to detect a position, a shape and an approximate depth of the thinner portions 8 and 8' on the inner surface 1b of the pipe 1 by means of the portions showing a higher temperature of the abovementioned thermal image.

Furthermore, the temperature of the portions of the outer surface 1a corresponding to the thinner portions 8 and 8' becomes lower than that of the portion of the outer surface 1a corresponding to the normal portion of the inner surface 1b as shown in FIG. 15, in the middle of the course of decrease of the temperature of the outer surface 1a to the original temperature thereof after the end of heating of the pipe 1 from the side of the inner surface 1b thereof, thus producing differences in temperature between these portions of the outer surface 1a.

While the above-mentioned differences in temperature still remain on the outer surface 1a of the pipe 1, the cuter surface 1a of the pipe 1 is shot by means of the thermal imaging system 4 to obtain a thermal image of the differences in temperature, which has portions showing a lower temperature, corresponding to the thinner portions 8 and 8' on the inner surface 1b of the pipe 1. The thus obtained thermal image is displayed on the monitor TV screen 5. Therefore, it is possible to detect the thinner portions 8 and 8' on the inner surface 1b of the pipe 1 by means of the above-mentioned thermal image.

It is possible to emphatically produce the above-mentioned differences in temperature $\Delta T$ and $\Delta T'$ between the portions of the outer surface 1a of the pipe corresponding to the thinner portions 8 and 8' on the inner surface 1b thereof, on the one hand, and the portion of the outer surface 1a of the pipe 1 corresponding to the normal portion of the inner surface 1b thereof, on the other hand, by cooling the pipe 1 from the side of the outer surface 1a thereof prior to the heating of the pipe 1 from the side of the inner surface 1b thereof in accordance with the sixth embodiment of the method of the present invention as described above. By shooting the outer surface 1a of the pipe 1 by means of the thermal imaging system 4 while the thus emphatically produced differences in temperature $\Delta T$ and $\Delta T'$ still remain on the outer surface 1a of the pipe 1, therefore, it is possible to detect more accurately the thinner portions 8 and 8' on the inner surface 1b of the pipe 1 in the form of a further clearer thermal image representing the differences in temperature $\Delta T$ and $\Delta T'$.

Figure 16:
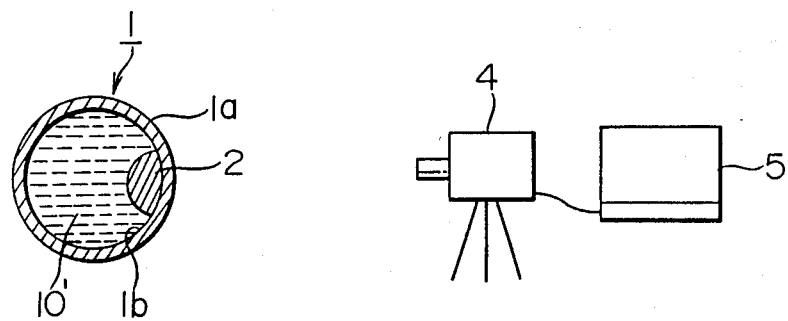
FIG. 16 is a schematic descriptive side view illustrating a seventh embodiment of the method of the present invention.

FIG. 16 is a schematic descriptive side view illustrating a seventh embodiment of the method of the present invention. As shown in FIG. 16, in the seventh embodiment of the method of the present invention, a pipe to be tested, the outer surface 1a of which is exposed, is cooled from the side of the inner surface 1b thereof so that a difference in temperature is produced between a portion of the outer surface 1a of the pipe 1 corresponding to an accumulation of foreign matters 2 as a defective portion on the inner surface 1b thereof, on the one hand, and a portion of the outer surface 1a of the pipe 1 corresponding to a normal portion of the inner surface 1b thereof, on the other hand.

Figures 17A, 17B:
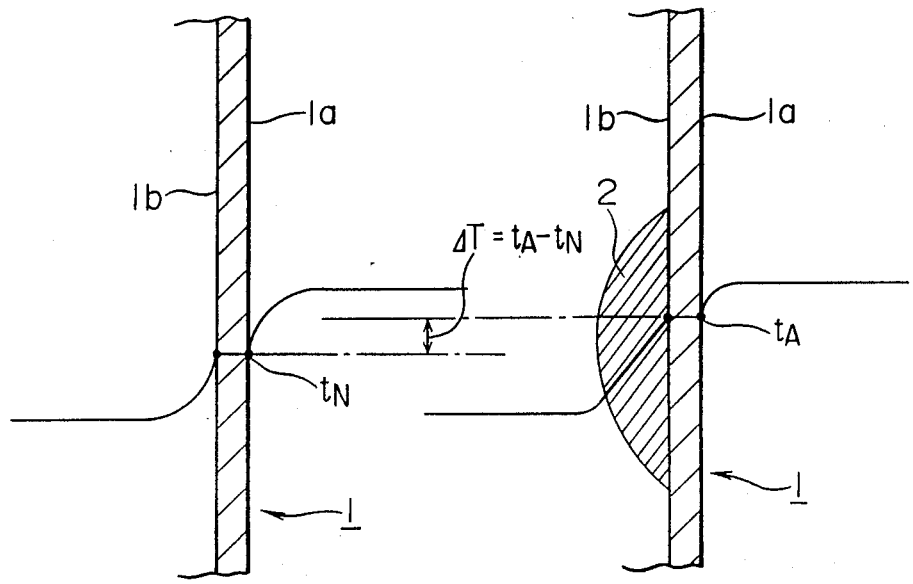
FIG. 17 (A) is a descriptive view illustrating a temperature of a portion of the outer surface of a pipe corresponding to a normal portion of the inner surface of the pipe cooled from the side of the inner surface thereof in accordance with the seventh embodiment of the method of the present invention as shown in FIG. 16.

FIG. 17 (A) is a descriptive view illustrating a temperature of a portion of the outer surface 1a of the pipe 1 corresponding to a normal portion of the inner surface 1b of the pipe 1 cooled from the side of the inner surface 1b thereof in accordance with the seventh embodiment of the method of the present invention, and FIG. 17 (B) is a descriptive view illustrating a temperature of a portion of the outer surface 1a of the pipe 1 corresponding to an accumulation of foreign matters 2 on the inner surface 1b of the pipe 1 cooled as mentioned above. As described above, the accumulation of foreign matters 2 on the inner surface 1b of the pipe 1 has a thermal conductivity lower than that of the normal portion of the pipe 1. Accordingly, because of the presence of the accumulation of foreign matters 2 having a lower thermal conductivity, a temperature of the portion of the outer surface la of the pipe 1 corresponding to the accumulation of foreign matters 2 on the inner surface 1b thereof decreases, by means of the above-mentioned cooling, more slowly than that of the portion of the outer surface 1a of the pipe 1 corresponding to the normal portion of the inner surface 1b thereof. As a result, as shown in FIGS. 17 (A) and 17 (B), the temperature $T_A$ of the portion of the outer surface 1a corresponding to the accumulation of foreign matters 2 on the inner surface 1b, after cooling for a certain period of time, is higher by $\Delta T$ than the temperature $t_N$ of the portion of the outer surface 1a corresponding to the normal portion of the inner surface 1b.

While the above-mentioned difference in temperature $\Delta T$ still remains on the outer surface 1a of the pipe 1, the outer surface 1a of the pipe 1 is shot by means of a thermal imaging system 4 to obtain a thermal image of the difference in temperature $\Delta T$, which has a portion showing a higher temperature, corresponding to the accumulation of foreign matters 2 on the inner surface 1b of the pipe 1. The thus obtained thermal image is displayed on a monitor TV screen 5. Therefore, it is possible to detect the accumulation of foreign matters 2 on the inner surface 1b of the pipe 1 by means of the above-mentioned thermal image. More specifically, it is possible to detect a position, a shape and an approximate thickness of the accumulation of foreign matters 2 on the inner surface 1b of the pipe 1 by means of the portion showing a higher temperature of the above-mentioned thermal image.

Cooling of the pipe 1 from the side of the inner surface 1b thereof is accomplished by passing a low-temperature fluid 10' such as a low-temperature liquid or gas through the pipe 1, or by inserting a cooling mechanism (not shown) into the pipe 1. When a low-temperature fluid 10' flows through the pipe 1, the pipe 1 may be cooled by the use of the flowing low-temperature fluid 10'.

It is possible to emphatically produce the above-mentioned difference in temperature $\Delta T$ between the portion of the outer surface 1a of the pipe 1 corresponding to the accumulation of foreign matters 2 on the inner surface 1b thereof, on the one hand, and the portion of the outer surface 1a of the pipe 1 corresponding to the normal portion of the inner surface 1b thereof, on the other hand, by heating the pipe 1 from the side of the outer surface 1a thereof prior to the cooling of the pipe 1 from the side of the inner surface 1b thereof in accordance with the seventh embodiment of the method of the present invention as described above. By shooting the outer surface 1a of the pipe 1 by means of the thermal imaging system 4 while the thus emphatically produced difference in temperature $\Delta T$ still remains on the outer surface 1a of the pipe 1, therefore, it is possible to detect more accurately the accumulation of foreign matters 2 on the inner surface 1b of the pipe 1 in the form of a further clearer thermal image representing the difference in temperature $\Delta T$.

Figure 18:
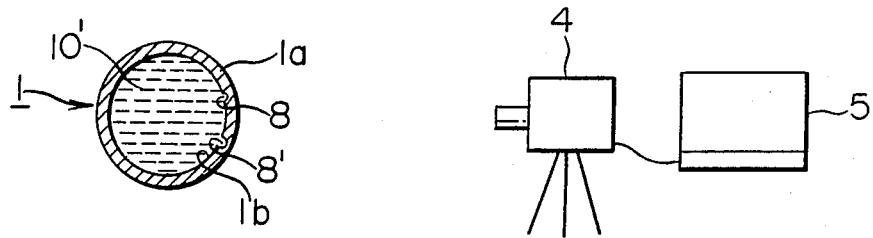
FIG. 18 is a schematic descriptive side view illustrating an eighth embodiment of the method of the present invention.

FIG. 18 is a schematic descriptive side view illustrating an eighth embodiment of the method of the present invention. As shown in FIG. 18, in the eighth embodiment of the method of the present invention, a pipe 1 to be tested, the outer surface 1a of which is exposed, is cooled from the side of the inner surface 1b thereof so that a difference in temperature is produced between portions of the outer surface 1a of the pipe 1 corresponding to thinner portions 8 and 8' as defective portions on the inner surface 1b thereof, on the one hand, and a portion of the outer surface 1a of the pipe 1 corresponding to a normal portion of the inner surface 1b thereof, on the other hand.

Figure 19:
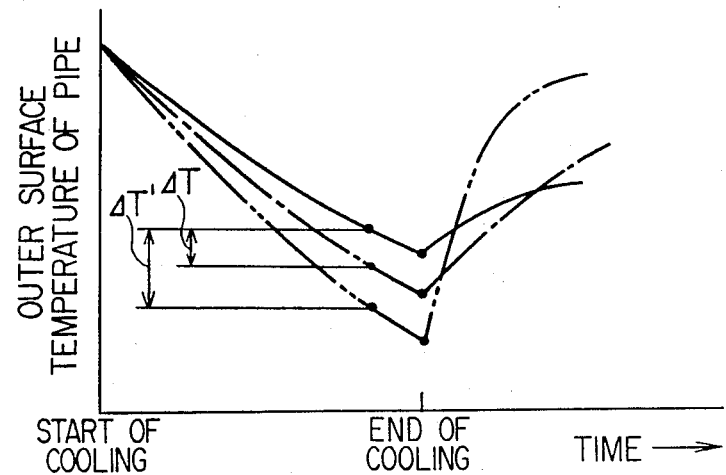
FIG. 19 is a graph illustrating changes in temperature, which are caused by cooling a pipe from e side of the inner surface thereof in accordance with the eighth embodiment of the method of the present invention as shown in FIG. 18, at a portion of the outer surface of the pipe corresponding to a normal portion of the inner surface thereof, and at a portion of the outer surface of the pipe corresponding to a thinner portion on the inner surface thereof.

FIG. 19 is a graph illustrating changes in temperature, which is caused by cooling the pipe 1 from the side of the inner surface 1b thereof in accordance with the eighth embodiment of the method of the present invention, at a portion of the outer surface 1a of the pipe 1 corresponding to a normal portion of the inner surface 1b thereof, and at a portion of the outer surface 1a of the pipe 1 corresponding to thinner portions 8 and 8' on the inner surface 1b thereof. As described above, the thinner portions 8 and 8' on the inner surface 1b of the pipe 1 have a thermal capacity smaller than that of the normal portion of the pipe 1. Accordingly, a temperature of the portions of the outer surface 1a of the pipe 1 corresponding to the thinner portions 8 and 8' on the inner surface 1b thereof decreases, by means of the above-mentioned cooling, more rapidly than that of the portion of the outer surface 1a of the pipe 1 corresponding to the normal portion of the inner surface 1b thereof. As a result, as shown in FIG. 19, during the period of time of from start to end of cooling and for certain period of time after the end of cooling, the temperature of the portion of the outer surface 1a corresponding to the shallower thinner portion 8 on the inner surface 1b, as represented by the one-point chain line, is lower by $\Delta T$ than the temperature of the portion of the outer surface 1a corresponding to the normal portion of the inner surface 1b, as represented by the solid line, and the temperature of the portion of the outer surface 1a corresponding to the deeper thinner portion 8' on the inner surface 1b, as represented by the two-point chain line, is lower by $\Delta T'$ than the temperature of the portion of the outer surface 1a corresponding to the normal portion of the inner surface 1b, as represented by the solid line. The difference in temperature $\Delta T'$ of the deeper thinner portion 8' from the normal portion is larger than the difference in temperature $\Delta T$ of the shallower thinner portion 8 from the normal portion.

While the above-mentioned differences in temperature $\Delta T$ and $\Delta T'$ still remain on the outer surface 1a of the pipe 1, the outer surface 1a of the pipe 1 is shot by means of a thermal imaging system 4 to obtain a thermal image of the differences in temperature $\Delta T$ and $\Delta T'$, which has portions showing a lower temperature, corresponding to the thinner portions 8 and 8' on the inner surface 1b of the pipe 1. The thus obtained thermal image is displayed on a monitor TV screen 5. Therefore, it is possible to detect the shallower thinner portion 8 and the deeper thinner portion 8' on the inner surface 1b of the pipe 1 by means of the above-mentioned thermal image. More specifically, it is possible to detect a position, a shape and an approximate depth of the thinner portions 8 and 8' on the inner surface 1b of the pipe 1 by means of the portion showing a lower temperature of the above-mentioned thermal image.

Furthermore, the temperature of the portions of the outer surface 1a corresponding to the thinner portions 8 and 8' becomes higher than that of the portion of the outer surface 1a corresponding to the normal portion of the inner surface 1b as shown in FIG. 19, in the middle of the course of increase of the temperature of the outer surface 1a to the original temperature thereof after the end of cooling of the pipe 1 from the side of the inner surface 1b thereof, thus producing differences in temperature between these portions of the outer surface 1a.

While the above-mentioned differences in temperature still remain on the outer surface 1a of the pipe 1, the outer surface 1a of the pipe 1 is shot by means of the thermal imaging system 4 to obtain a thermal image of the differences in temperature, which has portions showing a higher temperature, corresponding to the thinner portions 8 and 8' on the inner surface 1b of the pipe 1. The thus obtained thermal image is displayed on the monitor TV screen 5. Therefore, it is possible to detect the thinner portions 8 and 8' on the inner surface 1b of the pipe 1 by means of the above-mentioned thermal image. It is possible to emphatically produce the above-mentioned differences in temperature ΔT and ΔT' between the portions of the outer surface 1a of the pipe 1 corresponding to the thinner portions 8 and 8' on the inner surface 1b thereof, on the one hand, and the portion of the outer surface 1a of the pipe 1 corresponding to the normal portion of the inner surface 1b thereof, on the other hand, by heating the pipe 1 from the side of the outer surface 1a thereof prior to the cooling of the pipe 1 from the side of the inner surface 1b thereof in accordance with the eighth embodiment of the method of the present invention as described above. By shooting the outer surface 1a of the pipe 1 by means of the thermal imaging system 4 while the thus emphatically produced differences in temperature ΔT and ΔT' still remain on the outer surface 1a of the pipe 1, therefore, it is possible to detect more accurately the thinner portions 8 and 8' on the inner surface 1b of the pipe 1 in the form of a further clearer thermal image representing the differences in temperature ΔT and ΔT'.

Figure 20:
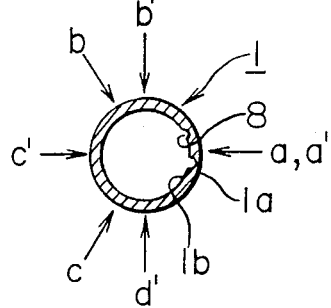
FIG. 20 is a schematic descriptive view illustrating detection of a defective portion on the inner surface of a pipe over the entire circumference of the inner surface in accordance with the method of the present invention.
Figure 21:
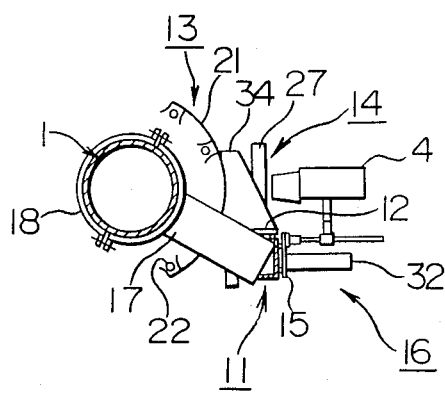
FIG. 21 is a schematic side view illustrating an embodiment of the apparatus of the present invention.
Figure 24:
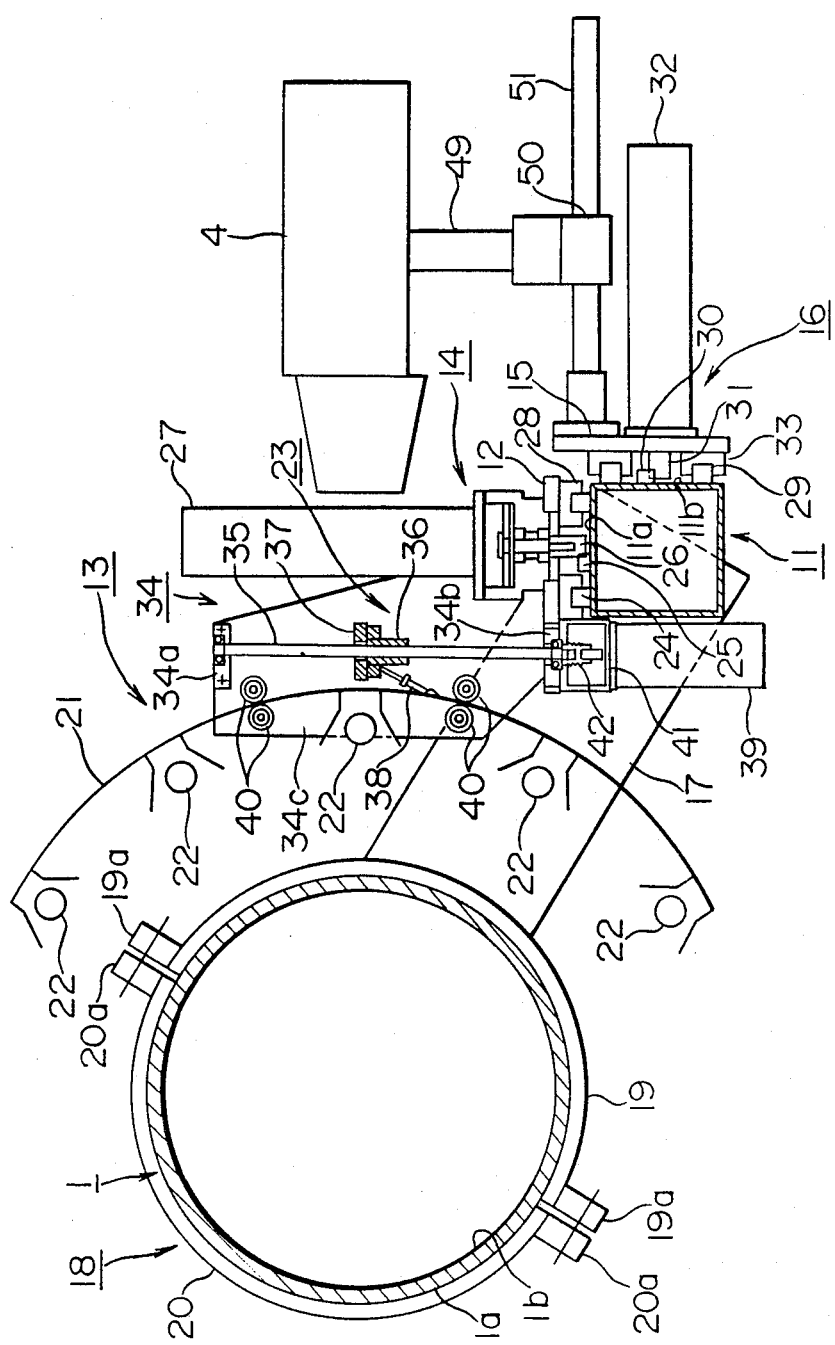
FIG. 24 is an enlarged side view illustrating the embodiment of the apparatus of the present invention as shown in FIG. 21.

In the above-mentioned first to eighth embodiments of the method of the present invention, in order to detect a thinner portion 8, for example, as the defective portion on the inner surface 1b of the pipe 1 over the entire circumference of the inner surface 1b thereof, it suffices, as shown by the arrows in FIG. 20, to sequentially shoot the outer surface 1a of the pipe 1 by means of the thermal imaging system 4 from three points a, b and c or four points a', b', c' and d' in the circumferential direction.

Now, an embodiment of the apparatus of the present invention is described with reference to FIGS. 21 to 25.

The apparatus of the present invention for detecting a defective portion on the inner surface of a pipe, the outer surface of which is exposed, comprises, as shown in FIGS. 21 to 25, a guide prop 11, having a square cross section and a prescribed length, fitted releasably to the outside of a pipe 1 to be tested, the outer surface of which is exposed, in parallel with the axis of the pipe 1; a first pedestal 12 movable along one surface 11a of the guide prop 11 in parallel with the axis of the pipe 1; a heating mechanism 13, mounted on the first pedestal 12, for heating the pipe 1 from the side of the outer surface 1a thereof; a first driving mechanism 14 for moving the first pedestal 12, together with the heating mechanism 13, along the surface 11a of the guide prop 11 in parallel with the axis of the pipe 1; a second pedestal 15 movable along another surface 11b of the guide prop 11 in parallel with the axis of the pipe 1; a thermal imaging system 4, mounted on the second pedestal 15 toward the pipe 1, for shooting the outer surface 1a of the pipe 1 heated by the heating mechanism 13 to provide a thermal image thereof; and a second driving mechanism 16 for moving the second pedestal 15, together with the thermal imaging system 4, along the another surface 11b of the guide prop 11 in parallel with the axis of the pipe 1.

The guide prop 11 comprises, for example, a square pipe made of aluminum. A band 18 comprising a pair of semi-annular fittings 19 and 20 for releasably fitting the guide prop 11 to the pipe 1 through an arm 17, is provided at each of the both ends of the guide prop 11. The guide prop 11 is releasably fitted to the pipe 1 to be tested, by putting the pipe 1 between the pair of fittings 19 and 20, and tightening flanges 19a and 20a formed at the both ends of each of the pair of fittings 19 and 20 toward each other by means of bolts and nuts.

The heating mechanism 13 mounted on the first pedestal 12 comprises a reflecting plate 21, having a concavely curved surface concentric with the pipe 1, directed toward the pipe 1; a plurality of heaters 22 provided on the concavely curved surface of the reflecting plate 21; and a reflecting plate driving mechanism 23 for return-moving the reflecting plate 21 along the direction of curvature thereof. The reflecting plate 21 comprises, for example, an aluminum sheet. A plurality of bar-shaped infrared heaters, for example, as the heaters 22, are provided at prescribed intervals on the concavely curved surface of the reflecting plate 21.

The first driving mechanism 14 comprises a first guide rail 24, provided on the one surface 11a of the guide prop 11 in parallel with the axis of the pipe 1, for guiding the first pedestal 12; a first rack 25 provided on the one surface 11a of the guide prop 11 in parallel with the first guide rail 24; a first pinion 26 engaging with the first rack 25; and a first motor 27, mounted on the first pedestal 12, for rotating the first pinion 26 to move the first pedestal 12 together with the heating mechanism 13 along the first guide rail 24 in cooperation with the first rack 25. A first guide element 28 engaging with the first guide rail 24 is provided on the lower surface of the first pedestal 1. The first pinion 26 engaging with the first rack 25 is fixed to the tip of a rotation axle of the first motor 27.

The second driving mechanism 16 comprises a second guide rail 29, provided on the another surface 11b of the guide prop 11 in parallel with the axis of the pipe, for guiding the second pedestal 15; a second rack 30 provided on the another surface 11b of the guide prop 11 in parallel with the second guide rail 29; a second pinion 31 engaging with the second rack 30; and a second motor 32, mounted on the second pedestal 15, for rotating the second pinion 31 to move the second pedestal 15 together with the thermal imaging system 4 along the second guide rail 29 in cooperation with the second rack 30. A second guide element 33 engaging with the second guide rail 29 is provided on the side of the second pedestal 15. The second pinion 31 engaging with the second rack 30 is fixed to the tip of a rotation axle of the second motor 32.

The reflecting plate driving mechanism 23 comprises a reflecting plate supporting frame 34, mounted on the first pedestal 12, for return-movably supporting the reflecting plate 21 along the direction of curvature thereof at the both ends thereof; a threaded rod 35, vertically and rotatably supported at an upper end thereof by an upper portion 34a of the reflecting plate supporting frame 34, and at a lower end thereof by a lower portion 34b of the reflecting plate supporting frame 34; a nut 36, having a connecting plate 37, screwengaging with the threaded rod 35; at least one connecting rod 38, one end of which is connected to the connecting plate 37 of the nut 36, and the other end of which is connected to the back of the reflecting plate 21; and a third motor 39, mounted on the first pedestal 12, for rotating the threaded rod 35 around the axis thereof to return-move the reflecting plate 21 along the direction of curvature thereof, in cooperation with the nut 36, the connecting plate 37, and the at least one connecting rod 38.

The reflecting plate supporting frame 34 has a plurality of pairs of guide rollers 40 at each of the both side portions 34c and 34d thereof, for holding each of the both ends of the reflecting plate 21 in between. The reflecting plate 21 is supported return-movably along the direction of curvature thereof by the plurality of pairs of guide rollers 40 at the both ends of the reflecting plate 21. The lower end of the threaded rod 35 passes through a lower portion 34b of the reflecting plate supporting frame 34 and projects downwardly therefrom. The lower end of the threaded rod 35 is connected to the rotation axle of the third motor 39 through a gear in a gear box 41 provided above the third motor 39. The threaded rod 35 rotates around the axis thereof clockwise and anticlockwise by the actuation of the third motor 39 to cause the nut 36, having the connecting plate 37, screw-connected with the threaded rod 35 to move up and down. As a result, the reflecting plate 21 is caused to return-move along the direction of curvature thereof by means of the at least one connecting rod 38, the one end of which is connected to the connecting plate 37 of the nut 36, and the other end of which is connected to the back of the reflecting plate 21.

Two guide bars 43 are vertically provided with the threaded bar 35 in between. Each of the guide bars 43 is fixed at an upper end thereof to the upper portion 34a of the reflecting plate supporting frame 34, and at a lower end thereof to the lower portion 34b of the reflecting plate supporting frame 34. A through-hole having a guide socket 44 is provided on each of the both end portions of the connecting plate 37, and each of the guide bars 43 is inserted into each of through-holes of the connecting plate 37. Therefore, the nut 36 and its connecting plate 37 move up and down along the threaded rod 35, while being guided by the guide bars 43, thus preventing swinging during vertical movement. A contact piece 45 of a limit switch for providing upper and lower limits of movement of the return-moving reflecting plate 21 is provided at one end of the connecting plate 37. An upper limit switch 46 and a lower limit switch 47 are provided respectively at positions where these limit switches come into contact with the contact piece 45 which moves vertically together with the connecting plate 37 The upper limit switch 46 and the lower limit switch 47 are secured to a supporting bar 48 which is fixed at an upper end thereof to the upper portion 34a of the reflecting plate supporting frame 34, and at a lower end thereof to the lower portion 34b of the reflecting plate supporting frame 34.

Figure 25:
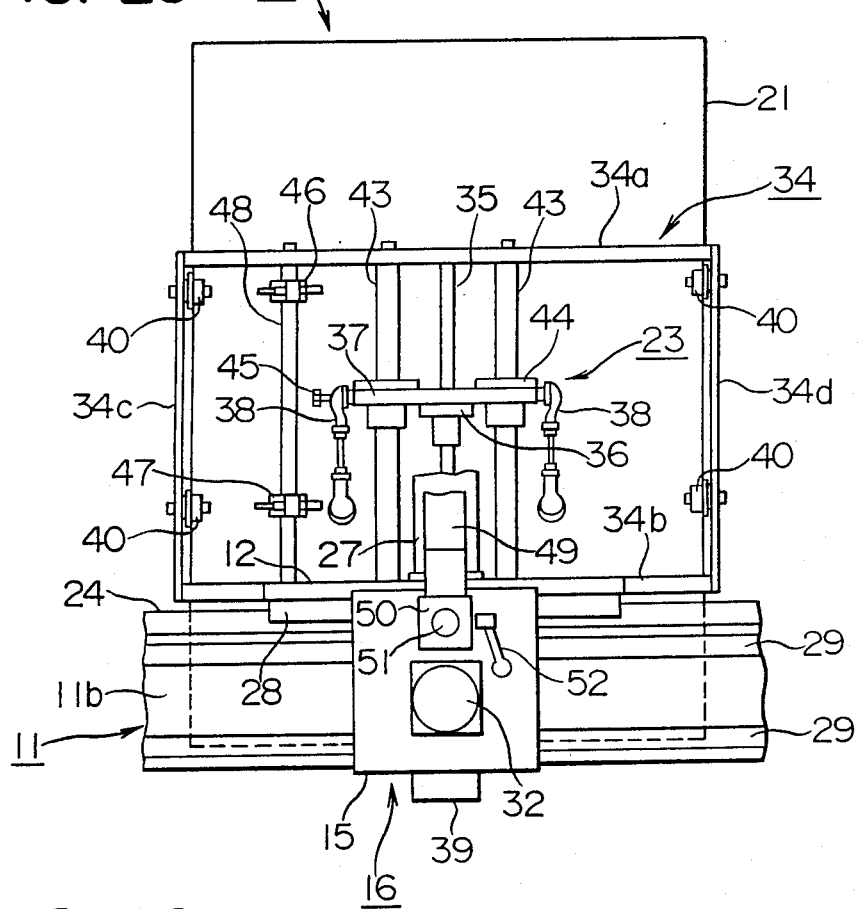
FIG. 25 is an enlarged rear view illustrating the embodiment of the apparatus of the present invention as shown in FIG. 21.

The thermal imaging system 4 is secured to the upper end of a supporting leg 49 having a fixing piece 50 at a lower portion thereof. A horizontal rod 51 for supporting the thermal imaging system 4 is fixed to a side of the second pedestal 15 so as to project horizontally from the side of the second pedestal 15. By inserting the horizontal rod 51 into the fixing piece 50 of the supporting leg 49, the thermal imaging system 4 is position-adjustably mounted on the second pedestal 15 toward the pipe 1. In FIG. 25, 52 indicates a handle for securing the supporting leg 49 of the thermal imaging system-4 to the horizontal rod 51.

According to the above-mentioned apparatus of the present invention, a defective portion on the inner surface 1b of the pipe 1, the outer surface of which is exposed, is detected as follows. The guide prop 11 is fitted releasably to the outside of the pipe 1 to be tested in parallel with the axis thereof by means of the band 18 provided at each of the both ends of the guide prop 11. The first motor 27 of the first driving mechanism 14 rotates the first pinion 26 to move the first pedestal 12, together with the heating mechanism 13, on the one surface 11a of the guide prop 11 along the first guide rail 24, in cooperation with the first rack 25. On the other hand, the third motor 39 of the reflecting plate driving mechanism 23 rotates the threaded rod 35 around the axis thereof to return-move the reflecting plate 21 along the direction of curvature thereof, in cooperation with the nut 36, the connecting plate 37 and the at least one connecting rod 38. More specifically, the first pedestal 12 moves, together with the heating mechanism 13, which comprises the reflecting plate 21, the heaters 22 and the reflecting plate driving mechanism 23, on the one surface 11a of the guide prop 11 along the first guide rail 24, thus causing the heating mechanism 13 to heat the pipe 1 from the side of the outer surface 1a thereof in the circumferential direction and in the longitudinal direction. Heating of the pipe 1 from the side of the outer surface 1a thereof by means of the heating mechanism 13 is accomplished so that a difference in temperature is produced between a portion of the outer surface 1a of the pipe 1 corresponding to a defective portion on the inner surface 1b thereof such as an accumulation of foreign matters or a thinner portion, on the one hand, and a portion of the outer surface 1a of the pipe corresponding to a normal portion of the inner surface 1b thereof, on the other hand.

On the other hand, the second motor 32 of the second driving mechanism 16 rotates the second pinion 31 to move the second pedestal 15 together with the thermal imaging system 4, on the another surface 11b of the guide prop 11 along the second guide rail 29, in cooperation with the second rack 30. The outer surface 1a of the pipe 1 is continuously shot in the circumferencial direction and in the longitudinal direction thereof by means of the thermal imaging system 4 while the above-mentioned difference in temperature still remains on the outer surface 1a of the pipe 1 to obtain a thermal image of the difference in temperature. By means of the thus obtained thermal image, it is possible to continuously detect defective portions such as an accumulation of foreign matters or a thinner portion on the inner surface 1b of the pipe 1, in the circumferential direction and in the longitudinal direction of the pipe 1. Driving and stoppage of the first motor 27 of the first driving mechanism 14, the second motor 32 of the second driving mechanism 16 and the third motor 39 of the reflecting plate driving mechanism 23 may be automatically conducted by a controller not shown. In order to detect the defective portions on the inner surface 1b of the pipe 1 over the entire circumference thereof, it suffices to loosen the bands 18 provided at the both ends of the guide prop 11, and cause the apparatus of the present invention to move in the circumferential direction of the pipe 1.

Now, an example of application of the method of the present invention is described with reference to the drawings.

EXAMPLE

Four circular thinner portions 8 having a diameter of 50 mm and a depth of 1 mm, 2 mm, 3 mm and 4 mm, respectively, were formed on the inner surface 1b of a pipe 1 made of steel having a diameter of 100 mm and a wall thickness of 5 mm, along the axis of the pipe 1. Detection of these four circular thinner portions 8 as the defective portions on the inner surface 1b of the pipe 1 was accomplished in accordance with the above-mentioned second embodiment of the method of the present invention. More particularly, as shown in FIG. 5, the pipe 1 was heated from the side of the outer surface 1a thereof by means of the heating mechanism 3 so that a difference in temperature is produced between the portions of the outer surface 1a of the pipe 1 corresponding to the thinner portions 8 as the defective portions on the inner surface 1b thereof, on the one hand, and the portion of the outer surface 1a of the pipe 1 corresponding to the normal portion of the inner surface 1b thereof, on the other hand. Then, the outer surface 1a of the pipe 1 was shot by means of the thermal imaging system 4 while the above-mentioned difference in temperature still remains on the outer surface 1a of the pipe 1 to obtain a thermal image 6 of the difference in temperature.

Figure 26:
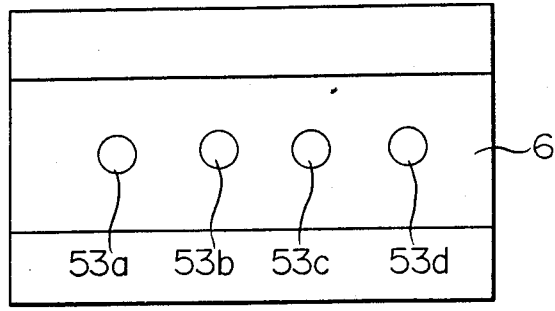
FIG. 26 is a descriptive view illustrating a thermal image obtained in an example of the method of the present invention.

FIG. 26 is a descriptive view of the thermal image 6 obtained as described above. As show in FIG. 26, the thermal image 6 of the difference in temperature on the outer surface 1a of the pipe 1 displayed a portion 53a showing a temperature corresponding to the thinner portion with a depth of 1 mm, a portion 53b showing a temperature corresponding to the thinner portion with a depth of 2 mm, a portion 53c showing a temperature corresponding to the thinner portion with a depth of 3 mm, and a portion 53d showing a temperature corresponding to the thinner portion with a depth of 4 mm. The portion 53a showing a temperature corresponding to the thinner portion with a depth of 1 mm was displayed in a color indicating a temperature higher than that of a portion of the outer surface 1a of the pipe 1 corresponding to the normal portion of the inner surface 1b thereof; the portion 53b showing a temperature corresponding to the thinner portion with a depth of 2 mm was displayed in a color indicating a temperature higher than that of the portion 53a showing a temperature corresponding to the thinner portion with a depth of 1 mm; the portion 53c showing a temperature corresponding to the thinner portion with a depth of 3 mm was displayed in a color indicating a temperature higher than that of the portion 53b showing a temperature corresponding to the thinner portion with a depth of 2 mm; and the portion 53d showing a temperature corresponding to the thinner portion with a depth of 4 mm was displayed in a color indicating a temperature higher than that of the portion 53c showing a temperature corresponding to the thinner portion with a depth of 3 mm. The portion 53d showing a temperature corresponding to the thinner portion with a depth of 4 mm was first displayed in the thermal image 6, and then, the portion 53c showing a temperature corresponding to the thinner portion with a depth of 3 mm, the portion 53b showing a temperature corresponding to the thinner portion with a depth of 2 mm, and the portion 53a showing a temperature corresponding to the thinner portion with a depth of 1 mm were sequentially displayed in this order in the thermal image 6. Thus, a position, a shape and an approximate depth of the thinner portions on the inner surface 1b of the pipe 1 could be detected by means of these portions 53a, 53b, 53c and 53d of the thermal image 6, which showed respective temperatures higher than that of the portion of the outer surface 1a of the pipe 1 corresponding to the normal portion of the inner surface thereof.

In the method of the present invention, the material of the pipe to be tested may be any of steel and other metals, plastics, concrete and others. The method of the present invention is applicable to any cross-sectional shape and size of the pipe to be tested. Furthermore, the method of the present invention is not limited to the detection of a defective portion on the inner surface of the pipe, but applicable to the detection of a defective portion on the inner surface of the side wall of a container, for example.

According to the present invention, as described above in detail, the following industrially useful effects are provided:

(1) By shooting the outer surface of a pipe to be tested by means of a thermal imaging system, a defective portion on the inner surface of the pipe is instantaneously displayed on a monitor TV screen. It is therefore possible to detect a defective portion on the inner surface of the pipe easily, rapidly and certainly.

(2) It is possible to detect a defective portion from a place apart from a pipe to be tested in a non-contact manner. It is not therefore necessary to provide a scaffold for detecting operation even when the pipe is installed at an elevated position apart from the ground.

(3) Handling of the thermal imaging system does not require a special qualification. There is therefore no limitation in personnel for the detection.

(4) The range of a single run of detection is relatively wide as compared with the conventional detection methods. A higher operating efficiency is therefore available.

(5) It is possible to detect a position, a shape and an approximate size of a defective portion, irrespective of the magnitude of the defective portion.

(6) A defective portion can be detected even on a pipe in service.

What is claimed is:

1. A method of detecting a defective portion, including either an accumulation of foreign matter or a thinned out region on the inner surface of a pipe, the outer surface of which is exposed, comprising:

selectivity heating or cooling a pipe, the outer surface of which is exposed, from the side of the outer surface of the pipe so that a difference in temperature is produced between a portion of the outer surface of said pipe corresponding to a defective portion, including either an accumulation of foreign matter or a thinned out region on the inner surface of the pipe, and a portion of the outer surface of said pipe corresponding to a normal portion of the inner surface thereof;

then shooting the outer surface of said pipe by means of a thermal imaging system while said difference in temperature still remains on the outer surface of said pipe to obtain a thermal image of said difference in temperature; and detecting said defective portion on the inner surface of said pipe by means of the thus obtained thermal image.

2. The method as claimed in claim 1, comprising:

heating said pipe from the side of the outer surface thereof so that a difference in temperature is produced between a portion of the outer surface of said pipe corresponding to said defective portion on the inner surface thereof and a portion of the outer surface of said pipe corresponding to said normal portion of the inner surface thereof; then obtaining said thermal image of said difference in temperature, which has a portion showing a higher temperature, corresponding to said defective portion on the inner surface of said pipe; and detecting said defective portion by means of said thermal image.

3. The method as claimed in claim 2, comprising: cooling said pipe from the side of the inner surface thereof, prior to said heating of said pipe from the side of the outer surface thereof.

4. The method as claimed in claim 1, comprising: cooling said pipe from the side of the outer surface thereof so that a difference in temperature is produced between a portion of the outer surface of said pipe corresponding to said defective portion on the inner surface thereof and a portion of the outer surface of said pipe corresponding to said normal portion of the inner surface thereof; then obtaining said thermal image of said difference in temperature, which has a portion showing a lower temperature, corresponding to said defective portion on the inner surface of said pipe; and detecting said defective portion by means of said thermal image.

5. The method as claimed in claim 4, comprising: heating said pipe from the side of the inner surface thereof, prior to said cooling of said pipe from the side of the outer surface thereof.

6. The method as claimed in claim 1, comprising: effecting said cooling of said pipe from the side of the outer surface thereof by spraying any one of a liquefied gas and a low-boiling-point liquid.

7. An apparatus for detecting a defective portion, including either an accumulation of foreign matter or a thinned out region on the inner surface of a pipe, the outer surface of which is exposed, comprising:

a guide prop (11), having a square cross section and a prescribed length, fitted releasably to the outside of a pipe, the outer surface of which is exposed, in parallel with the axis of the pipe;

a first pedestal (12) movable along one surface (11a) of said guide prop (11) in parallel with the axis of said pipe;

a heating mechanism (13), mounted on said first pedestal (12), for heating said pipe from the side of the outer surface of the pipe, said heating mechanism (13) comprising a reflecting plate (21), having a concavely curved surface concentric with said pipe, and directed toward said pipe a plurality of heaters (22) provided on said concavely curved surface of said reflecting plate (21), and a reflecting plate driving mechanism (23) for return-moving said reflecting plate (21) along the direction of curvature thereof;

a first driving mechanism (14) for moving said first pedestal (12), together with said heating mechanism (13), along said one surface (11a) of said guide prop (11) in parallel with the axis of said pipe;

a second pedestal (15) movable along another surface (11b) of said guide prop (11) in parallel with the axis of said pipe;

a thermal imaging system (b 4), mounted on s-id second pedestal (15) toward said pipe, for shooting the outer surface of said pipe heated by said heating mechanism (13) to obtain a thermal image of said outer surface; and a second driving mechanism (16) for moving said second pedestal (15), together with said thermal imaging system (b 4), along said another surface (11b) of said guide prop (11) in parallel with the axis of said pipe.

8. The apparatus as claimed in claim 7, wherein: said first driving mechanism (14) comprises: a first guide rail (24), provided on said one surface (11a) of said guide prop (11) in parallel with the axis of said pipe, for guiding said first pedestal (12);

a first rack (25) provided on said one surface (11a) of said guide prop (11) in parallel with said first guide rail (24);

a first pinion (26) engaging with said first rack (25); and a first motor (27), mounted on said first pedestal (12), for rotating said first pinion (26) to move said first pedestal (12) together with said heating mechanism (13) along said first guide rail (24) in cooperation with said first rack (25), said first pinion (26) being fixed to the tip of a rotation axle of said first motor (27).

9. The apparatus as claimed in claim 7, wherein said second driving mechanism (16) comprises:

a second guide rail (29), provided on said another surface (11b) of said guide prop (11) in parallel with the axis of said pipe, for guiding said second pedestal (15);

a second rack (30) provided on said another surface (11b) of said guide prop (11) in parallel with said second guide rail (29);

a second pinion (31) engaging with said second rack (30); and a second motor (32), mounted on said second pedestal (15), for rotating said second pinion (31) to move said second pedestal (15) together with said thermal imaging system (b 4) along said second guide rail (29) in cooperation with said second rack (30), said second pinion (31) being fixed to the tip of a rotation axle of said second motor (32).

10. The apparatus as claimed in claim 7, wherein: said reflecting plate driving mechanism (23) comprises:

a reflecting plate supporting frame (34), mounted on said first pedestal (12), for return-movably supporting said reflecting plate (21) along the direction of curvature thereof at the both ends thereof, said reflecting plate supporting frame (34) having a plurality of pairs of guide rollers (40) at each of the both side portions (34c, 34d) thereof, for holding each of said both ends of said reflecting plate (21) in between;

a threaded rod (35), vertically and rotatably supported at an upper end thereof by an upper portion (34a) of said reflecting plate supporting frame (34), and at a lower end thereof by a lower portion (34b) of said reflecting plate supporting frame (34);

a nut (36), having a connecting plate (37), screw-engaging with said threaded rod (35);

at least one connecting rod (38), one end of which is connected to said connecting plate (37) of said nut (36), and the other end of which is connected to the back of said reflecting plate (21); and a third motor (39), mounted on said first pedestal (12), for rotating said threaded rod (35) around the axis thereof to return-move said reflecting plate (21) along the direction of curvature thereof, in cooperation with said nut (36), said connecting plate (37) and said at least one connecting rod (38).

* * * * *